(12) United States Patent
Sala

(10) Patent No.: US 7,371,585 B2
(45) Date of Patent: May 13, 2008

(54) MEMBRANES INCORPORATING RECOGNITION MOIETIES

(75) Inventor: Rafael Fernando Sala, Mountain View, CA (US)

(73) Assignee: Genencor International, Inc., Palo Alto, CA (US)

( * ) Notice: Subject to any disclaimer, the term of this patent is extended or adjusted under 35 U.S.C. 154(b) by 484 days.

(21) Appl. No.: 11/024,571

(22) Filed: Dec. 28, 2004

(65) Prior Publication Data

US 2005/0250128 A1 Nov. 10, 2005

Related U.S. Application Data

(60) Provisional application No. 60/533,672, filed on Dec. 31, 2003.

(51) Int. Cl.
*G01N 33/543* (2006.01)
(52) U.S. Cl. ............... 436/518; 435/287.1; 435/287.2; 436/528
(58) Field of Classification Search ............... None
See application file for complete search history.

(56) References Cited

U.S. PATENT DOCUMENTS

| 5,401,378 A | 3/1995 | King et al. |
| 5,443,955 A | 8/1995 | Cornell et al. |
| 5,741,409 A | 4/1998 | Raguse et al. |
| 5,741,712 A | 4/1998 | Cornell et al. |
| 5,753,093 A | 5/1998 | Raguse et al. |
| 5,874,316 A | 2/1999 | Cornell et al. |
| 6,291,155 B1 | 9/2001 | Raguse et al. |
| 6,316,273 B1 | 11/2001 | King et al. |

FOREIGN PATENT DOCUMENTS

| WO | WO 98/55853 | 12/1998 |
| WO | WO 00/47548 | 8/2000 |
| WO | WO 02/079394 | 10/2002 |

*Primary Examiner*—Christopher L. Chin
(74) *Attorney, Agent, or Firm*—Howrey LLP; Viola T. Kung

(57) ABSTRACT

The present invention provides a thiosulfonate-activated ionophore comprising an ionophore, a spacer group, and an alkylthiosulfonate moiety. A preferred ionophore is gramicidin A. A preferred alkylthiosulfonate is methanethiosulfonate. The present invention also provides a conjugate comprising an ionophore, a spacer group, and a recognition molecule. Further the invention related to membranes incorporating the conjugates and biosensors comprising said membranes.

9 Claims, 11 Drawing Sheets

MEMBRANES INCORPORATING RECOGNITION MOIETIES

This application claims priority to U.S. provisional application No. 60/533,672, filed Dec. 31, 2003. The content of which is incorporated herein by reference in its entirety.

FIELD OF THE INVENTION

The present invention relates to a thiosulfonate-activated ionophore. The present invention also relates to a conjugate comprising an ionophore, a spacer group, and a recognition molecule, wherein the spacer group covalently links the ionophore to the recognition molecule. The present invention further relates to membranes having recognition molecules attached to ionophores and biosensors comprising such membranes.

BACKGROUND OF THE INVENTION

Ion channels are ionophores that play an essential role in the movement of ions across cell membranes. Membranes are lipid bilayers and they build a hydrophobic, low dielectric barrier to hydrophilic and charged molecules. Charged molecules or atoms cannot penetrate this barrier. Ion channels provide a high conducting, hydrophilic pathway across the hydrophobic interior of the membrane. A well-known example of an ion channel molecule (or ionophore) is the polypeptide gramicidin, a naturally occurring antibiotic known to insert in biological membranes and to form transient dimers that facilitate the flux of ions through biological membranes.

A biosensor is a device for detecting a biologically active analyte. One type of biosensor is an immunosensing device based on an electrical detection of open ion channels. An example of this type of biosensor is the ICS Biosensor disclosed by Australian Membrane and Biotechnology Research Institute (where ICS is ion channel switch) (WO 98/55853). In the presence of an applied potential, ions flow between a reservoir and an external compartment when the ion channels are open. Recognition molecules specific for a desired analyte (typically fragmented antibodies) are linked to mobile gramicidin monomers in the outer leaflet of the bilayer. When an analyte is present and binds to the recognition molecule, the mobile gramicidin becomes crosslinked, preventing the formation of a conductive dimeric state with the tethered gramicidin channels in the inner half of the membrane. This crosslinking closes off open channels, which results in a reduction on the impedance current.

The current technology for the attachment of recognition moieties to gramicidin relies on a non-covalent complexation or association between biotin and streptavidin. Both gramicidin and the recognition molecule are chemically derivatized to contain a terminal biotin moiety. Addition of streptavidin produces a non-covalent mediated linkage between gramicidin and the recognition moiety by forming a ternary complex with streptavidin. (U.S. Pat. Nos. 5,874,316; 5,443,995; 5,753,093; 5,741,409; and 5,874,316).

The association between biotin and streptavidin is subject to a number of limitations that reduce the effectiveness of the biosensor. For example, the biotin and streptavidin system are subject to dissociation characterized by the kinetic rate constant, $k_{off}$. This limitation is accentuated due to the low concentration of components in the biosensor such that the association ($k_{on}$) of the biotinylated species to streptavidin is disfavored. This dissociation contributes to a relatively short stability of the biosensor (days instead of months) when stored in hydrated form and decreases the overall sensor performance.

Furthermore, the addition of streptavidin to the biotinylated gramicidins and transmembrane lipids results in an aggregation or "streptavidin gating" that reduces the admittance. In some cases, admittance may be reduced by a factor of approximately 2-20. It would be desirable to avoid the signal and sensitivity loss associated with streptavidin gating.

General biosensor and membrane technology and particularly ion-channel switch biosensors are described in U.S. Pat. Nos. 5,443,955; 5,741,409, and 5,741,712; the contents of which are incorporated herein by reference.

WO 02/079394 discloses a method of producing a glycoprotein by reacting a protein with a glycosylated methanethiosulfonate reagent under conditions effective to produce a glycoprotein. The glycoprotein has altered functional characteristics when compared with the protein.

There is a need for an improved method of associating ionophores to recognition molecules. Additionally, there is a need for biosensors that are more stable and have better performance.

SUMMARY OF THE INVENTION

The present invention is directed to a thiosulfonate-activated ionophore comprising an ionophore, a spacer group, and an alkylthiosulfonate moiety, wherein the spacer group covalently links the ionophore to the alkylthiosulfonate moiety.

Ionophores suitable for the present invention include gramicidin, band three protein, bacteriorhodopsin, proteorhodopsin, mellitin, alamethicin, an alamethicin analogue, porin, tyrocidine, tyrothricin, and valinomycin. A preferred ionophore is gramicidin A (gA). A preferred alkylthiosulfonate is methanethiosulfonate.

The spacer group is selected from the group consisting of alkyl, alkyl amides, alkyl esters, alkyl carbamates, alkyl carbonates, oligomers of alkylidene glycol (such as ethylene glycol), combinations of oligomers of ethylene glycol with amides, esters or carbamates, and oligopeptides.

The present invention is also directed to a conjugate comprising an ionophore, a spacer group, and a recognition molecule, wherein the spacer group covalently links the ionophore to the recognition molecule and the spacer group is linked to the recognition molecule via a disulfide bond. Recognition molecules, for example, include antibodies, antibody fragments, enzymes, enzyme inhibitors, antigens, lectins, haptens, aptamers, chelating agents and dyes.

The present invention provides a membrane in which the admittance of the membrane is dependent on the presence or absence of an analyte. The membrane comprises a first and a second layer each comprising closely packed amphiphilic molecules; a plurality of first ionophores and second ionophores; and a plurality of recognition molecules covalently attached to the second ionophores via a disulfide bond and a spacer group, the recognition molecules being capable of binding to the analyte. In the membrane, the first ionophores are fixed in the first layer and are prevented from lateral diffusion in the first layer; and the second ionophores are located in the second layer and are capable of lateral diffusion within the second layer. The binding of the analyte to the recognition molecules causes a change in the relationship between the first ionophores and the second ionophores such that the flow of ions across the membrane via the first and the second ionophores is allowed or prevented.

The present invention further provides a biosensor comprising the membrane and a solid conducting surface, and a device comprising an array of such biosensors. The biosensors are useful for detecting the presence or absence of an analyte in a sample.

DETAILED DESCRIPTION OF THE PREFERRED EMBODIMENTS

Figure 1:
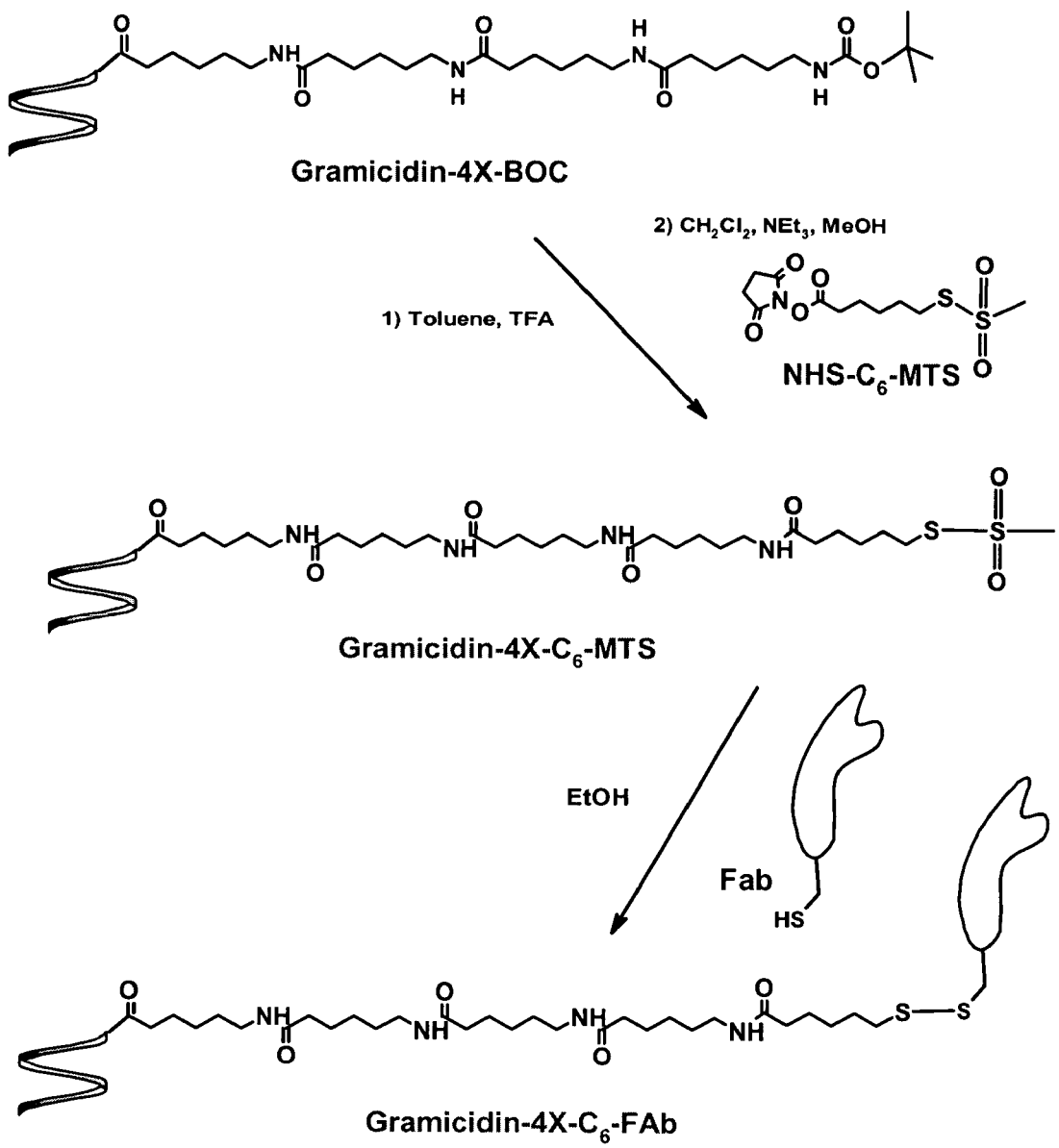
FIG. 1 illustrates the formation of gramicidin-4X-$C_6$-Fab from gramicidin-4X-BOC and NHS-$C_6$-MTS.

In order to provide a clear and consistent understanding of the specification and claims, including the scope given to such terms, the following definitions are provided:

As used herein, "admittance" refers to an electrical term used to describe the ability of ions to transverse a system when a potential is applied, and is expressed as units of Siemen (S) or Mho (inverse of Ohm). Admittance is the reciprocal of impedance.

As used herein, "an amphiphilic molecule" refers to a molecule having a hydrophilic head portion and one or more hydrophobic tails.

As used herein, "an antibody fragment" is part of an antibody that contains at least one antigen-binding site and is capable of binding to the antigen. Preferred antibody fragments include fragment antigen binding Fab' and $F(ab')_2$.

As used herein, "impedance" is a general expression applied to any electrical entity that impedes the flow of ions. Impedance is used to denote a resistance, a reactance, or a combination of both reactance and resistance, with units of Ohm (Ω).

As used herein, "phase" refers to the delay between applying a voltage and measuring the current in an electrical circuit.

As used herein, "reactance" refers to the property of resisting or impeding the flow of ions (AC current or AC voltage) in inductors and capacitors, with units of Ohm (Ω).

As used herein, "ionophores" refer to natural or synthetic substances that promote the passage of ions through lipid barriers in natural or artificial membranes. Ionophores may form ion-conducting pores in membranes.

As used herein, "a spacer group" is a chemical group that links an ionophore and a reactive moiety. In preferred embodiments, the reactive moiety is exposed on the exterior of a membrane and optimally reacts with a recognition molecule without steric hindrance.

As used herein, "thiosulfonate-activated ionophore" comprises an ionophre, a spacer group and a reactive or active alkylthiosulfonate moiety.

As used herein, "a recognition molecules" is a molecule that contains a recognition moiety that can bind with some specificity to a desired analyte (target molecule). Recognition molecules in general have one or more sulfhydryl groups.

The present invention is directed to an activated ionophore comprising an ionophore, a spacer group, and a reactive moiety. The present invention is also directed to a conjugate comprising an ionophore, a spacer group, and a recognition molecule, wherein the spacer group covalently links the ionophore to the recognition molecule and the spacer group is linked to the recognition molecule through a disulfide bond. The present invention is further directed to a membrane inserted with such a conjugate in which the admittance of the membrane is dependent on the presence or absence of an analyte.

Ionophores of the present invention are in general peptides capable of forming helices and aggregates thereof, podands, coronands and cryptands. Podands, cryptands and coronands have been described previously in the scientific literature (see, for example, V. F. Kragten et al., *J. Chem. Soc. Chem. Commun.*, 1985, 1275; O. E. Sielcken, et al., *J. Amer. Chem. Soc.*, 1987, 109 4261; and J. G. Neevel, et al., *Tetrahedron Letters*, 1984, 25, 2263). It is preferred that the ionophore is a peptide capable of forming a helix or aggregates thereof.

Peptides that form α helices generally need to exist as aggregates in the membrane to form ionophores. Typically, the α helical peptides arrange to form aggregates in such a manner that an ionophore is created through the aggregate. It is preferred that the ionophore is a peptide that forms a β helix.

Ionophores useful for the present invention include both transmembrane and dimeric ionophores, such as gramicidin, band three protein (*Cell Mol. Biol.*, 2004; 50(2):117-38), bacteriorhodopsin (*Ann. Rev. Biophys. Biomol. Struct.*, 1999; 28:367-99) proteorhodopsin (*EMBO Journal*, 2003; 22:1725-1731), mellitin (*Biochem. Biophys. Acta*, 1983; 732 668-674), alamethicin (*Journal of Lipid Research*, 1973; 14: 255-a-257), an alamethicin analogue, porin (*PNAS*, 2002; 99:13108-13113), tyrocidine (*J. Biol. Chem.* 1979; 254: 6278-6287), tyrothricin (*European Journal of Clinical Microbiology & Infectious Diseases*, 1996; 15: 261-263) and valinomycin (*Journal of General Physiology*, 1981; 77:387-417).

Gramicidins include gramicidin A, gramicidin B, gramicidin C, gramicidin D, gramicidin GT, gramicidin GM, gramicidin GM⁻, gramicidin GN⁻, and gramicidin A'. Gramicidin A is particularly useful in the present invention.

Gramicidin A is a peptide that forms a β helix. The primary sequence of gramicidin A is described in U.S. Pat. No. 5,741,712. Gramicidin A is produced either synthetically or extracted from *Bacillus brevis*. Gramicidin A functions as a polar channel that traverses non-polar biological membranes. In phospholipid bilayers, gramicidin A is believed to exist as a helical dimer, which substantially partitions into the hydrophobic region of the bilayer. When it is desired to cross-link the amphiphilic molecules and the gramicidin A, gramicidin A may be modified by replacing one, two, three or four tryptophan groups in the gramicidin A with a polymerizable group, such as styrene. The polymerizable group is attached to the alpha carbon of the 9, 11, 13 and/or 15th amino acid residue of the native gramicidin A.

In one embodiment of the invention, the invention is directed to an activated ionophore comprising an ionophore and a linker molecule that contains a spacer group and a reactive moiety, wherein the spacer group covalently links the ionophore to the reactive moiety. Suitable reactive groups include, but are not limited to, alkylthiosulfonate, vinyl sulfone, oxiranes, aziridines, thiiranes, pyridylsulfides, haloacetimide, haloacetamides, and maleimide groups. Some of these reactive groups are described in Greg Hermanson, *Bioconjugate Techniques,* Academic Press (1996). Other reactive groups include N-hydroxysuccinimide esters or other activated esters for covalent coupling to amine groups on proteins, and hydrazine derivatives for coupling onto oxidized sugar residues. A reactive group of particular interest is an alkylthiosulfonate.

In a preferred embodiment of the invention, the invention is directed to a thiosulfonate-activated ionophore comprising an ionophore, a spacer group, and an alkylthiosulfonate moiety, wherein the spacer group covalently links the ionophore to the alkylthiosulfonate moiety. Alkylthiosulfonates useful for the present invention are $C_1$-$C_6$ alkylthiosulfonates, cyclicalkythiosulfonates, and phenylthiosulfonates and derivatives thereof. Non-limiting examples include methanethiosulfonate (MTS), ethanethiosulfonate, and propanethiosulfonate, with methanethiosulfonate being preferred.

The spacer group can be hydrophilic (having a tendency to bind or absorb water) or hydrophobic (antagonistic to water and incapable of dissolving in water). The spacer group of the present invention is selected from the group consisting of saturated or unsaturated $C_{1-8}$ alkyl, saturated or unsaturated $C_{3-7}$ cycloalkyl, aryl, aralkyl, heteroaryl, and saturated or unsaturated $C_{2-6}$ heterocycle; $C_{1-8}$ alkylamides, $C_{1-8}$ alkylesters, $C_{1-8}$ alkylcarbamates, $C_{1-8}$ alkylcarbonates, oligomers (e.g., n=2-10) of alkylidene glycol (such as ethylene glycol), combinations of oligomers of ethylene glycol with amides, esters or carbamates, and oligopeptides, where in all rings or chains optionally bear one or more desired substituents such as halogen, hydroxy, $C_{1-4}$ alkoxy, carboxy, cyano, nitro, sulfonamido, sulfonate, phophate, amino and substituted amino. In some embodiments the spacer group is a $C_{1-8}$ alkyl, an oligomer of alkylideneglycol, or oligomers of ethylene glycol with amides, esters or carbamates.

Figure 4:
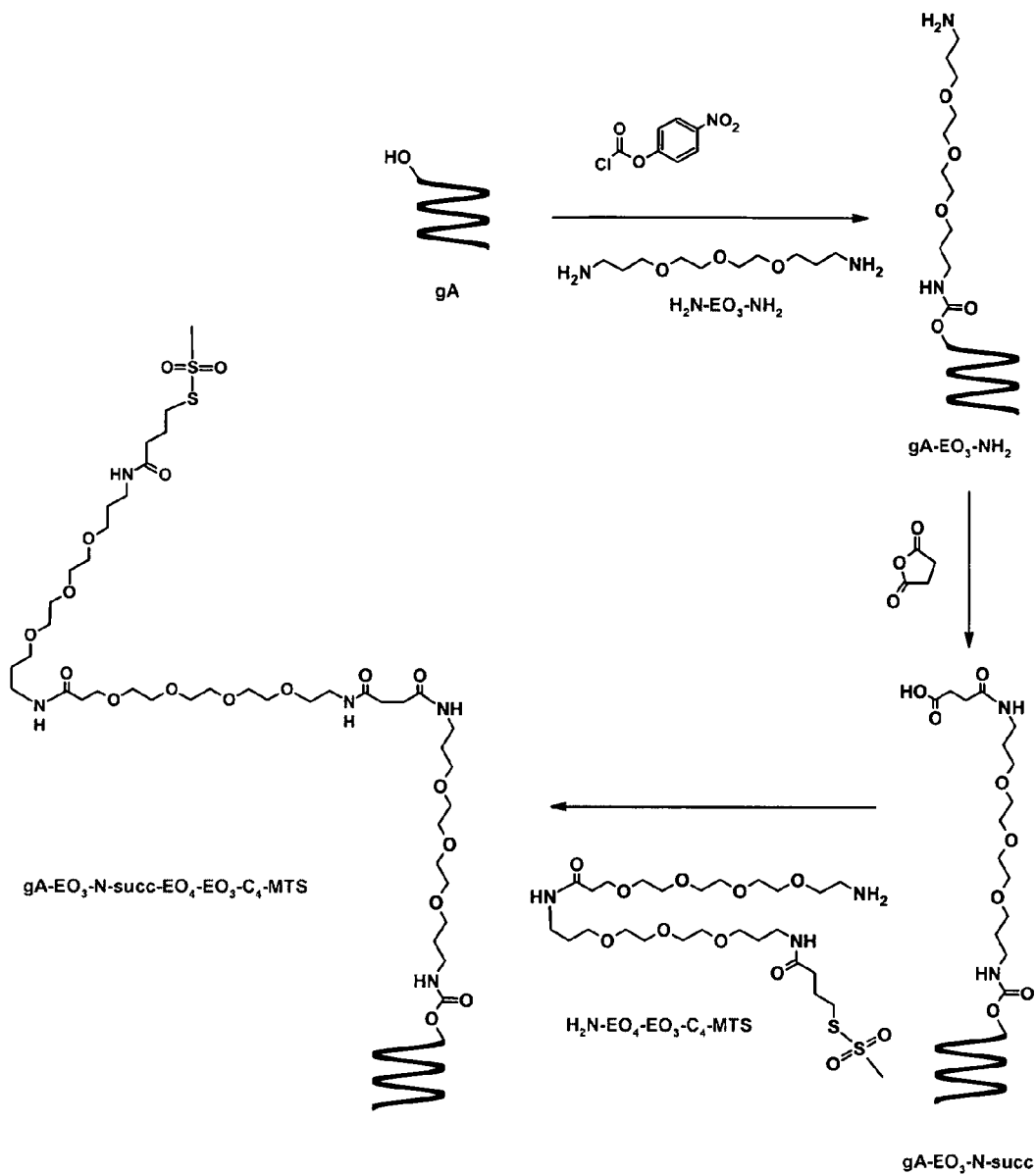
FIG. 4 illustrates the scheme for the preparation of a thiosulfonate-activated ionophore, gA-$EO_3$-N-succ-$EO_4$-$EO_3$-$C_4$-MTS.

The ionophore and the spacer group can be linked by any suitable moiety such as an ester, amide, carbamate, carbonate, or the like. In one embodiment of the invention, the spacer group is covalently linked to the ionophore through a carbamate group. In another embodiment of the invention, the spacer group is covalently linked to the ionophore through an ester group. Examples of thiosulfonate-activated ionophores include gramicidin-X-$C_b$-MTS; wherein X is aminocaproyl, and $C_b$ is alkylcarbonyl, with alkyl being $C_{1-10}$, preferably $C_{2-8}$, more preferably $C_{4-6}$. A specific example of a thiosulfonate-activated ionophore is gramicidin-4X-$C_6$-MTS, wherein X is aminocaproyl (—NH(CH$_2$)$_5$COO—), and $C_6$ is pentylcarbonyl (—(CH$_2$)$_5$CO—). Another specific example of a thiosulfonate-activated ionophore is gramicidin-EO$_3$-N-succ-EO$_4$-EO$_3$-C$_4$-MTS, wherein $C_4$ is propanylcarbonyl (—(CH$_2$)$_3$CO—), EO is ethylene oxide (—(CH$_2$)$_2$O—), and succ is succinate (OCCH$_2$CH$_2$CO). The chemical structures of gramicidin-4X-$C_6$-MTS and gramicidin-EO$_3$-N-succ-EO$_4$-EO$_3$-C$_4$-MTS are illustrated in FIGS. 1 and 4, respectively.

Figure 2:
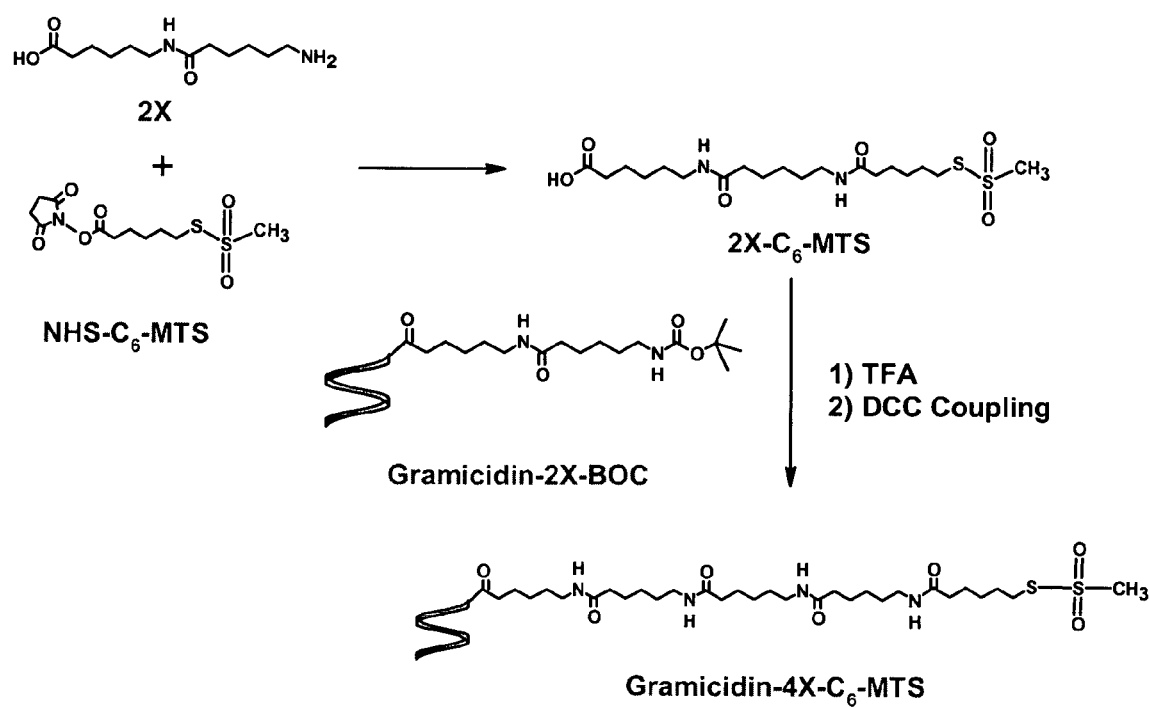
FIG. 2 illustrates the formation of gramicidin-4X-$C_6$-MTS from gramicidin-2X-BOC and 2X-$C_6$-MTS.

The starting material for preparing an ionophore-spacer compound, for example, gramicidin-nX-BOC (X=aminocaproyl; BOC=t-butyl-oxy-carbonyl, a protecting group, n=1-20) can be made in accordance with the procedures described in U.S. Pat. Nos. 6,210,551; 5,874,316; 5,766,960; 5,693,477; 5,741,712; or 5,436,170; or in European Patent No. EP 0455705 B1 or EP 0432188 B1; the contents of which are incorporated herein by reference. The chemical structure of Gramicidin-4X-BOC, (O-(N-(N-(N-BOC-6-aminocaproyl)-6-aminocaproyl)-6-aminocaproyl)gramicidin) is shown in FIG. 1, and the chemical structure of gramicidin-2X-BOC is shown in FIG. 2.

The thiosulfonate-activated ionophores can be prepared by modifying an ionophore-spacer compound to bear a reactive group in any suitable manner. For example, a reactive group can be incorporated at the end of the spacer molecule by a suitable coupling reaction.

In one embodiment, the spacer and the ionophore are linked by an ester moiety. As shown in Scheme 1 and FIG. 1, after deprotection of the protecting group (BOC), gramicidin-4X-BOC is coupled with N-succinimidyloxycarbonylpentyl methanethiosulfonate (NHS-$C_6$-MTS) to form gramicidin-4X-$C_6$-MTS.

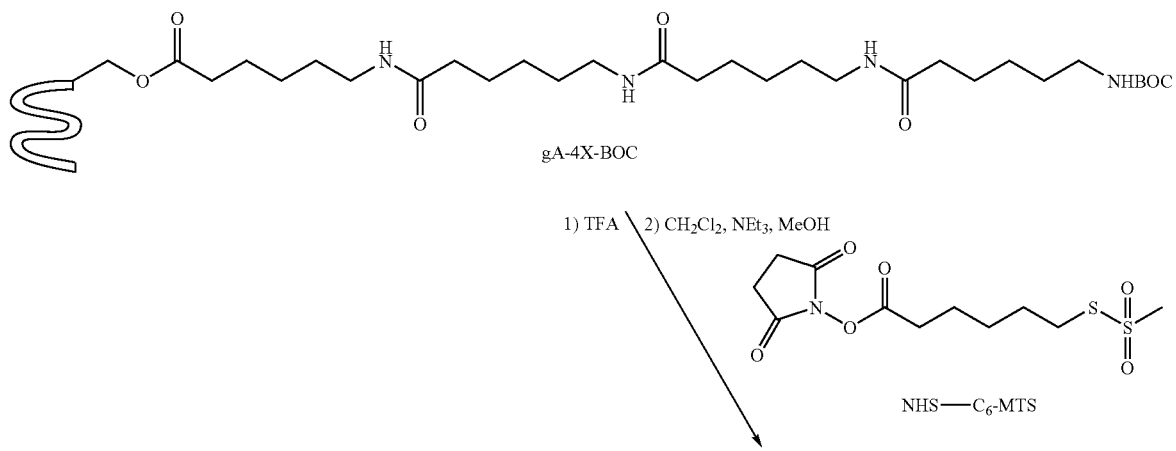

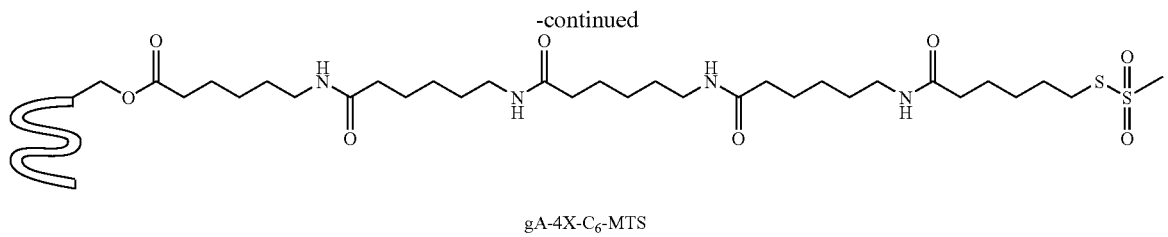

gA-4X-C$_6$-MTS

Alternatively, as shown in Scheme 2, gramicidin-4X-BOC can be deprotected and coupled to 6-carboxyhexyl methanethiosulfonate (C$_6$-MTS) by known carbodiimide assisted coupling to form gramicidin-4X-C$_6$-MTS.

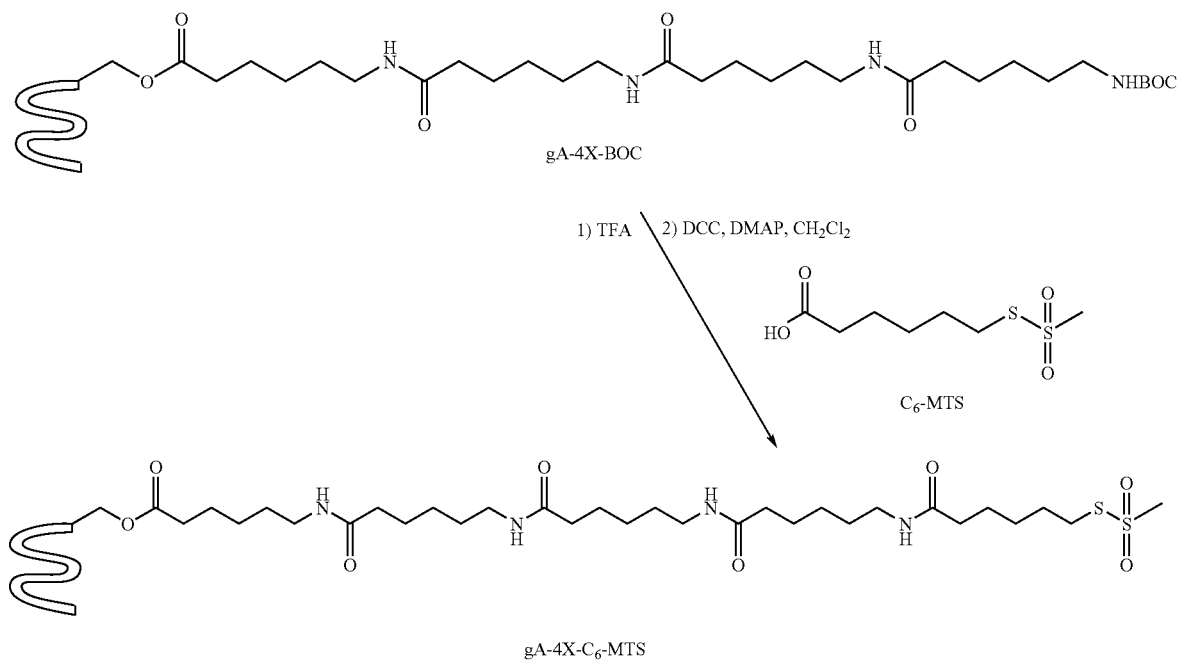

Similarly, as shown in FIG. 2, gramicidin-2X-BOC may be reacted with N-(N-(N-6-carbonylpentylmethanethiosulfonate)-6-aminocaproyl)-6-aminocaproic acid (2X-C$_6$-MTS) species to form gramicidin-4X-C$_6$-MTS. The reaction can be carried out by deprotecting gramicidin-2X-BOC with trifluoroacetic acid (TFA) and subsequently adding it to the 2X-C$_6$-MTS with 1M N,N'-dicyclohexylcarbodiimide solution in dichloromethane (DCC in CH$_2$Cl$_2$) and with 4-(dimethylamino)-pyridine (DMAP) to form gramicidin-4X-C$_6$-MTS.

In another embodiment, the spacer and the ionophore are linked by a carbamate moiety. A particular example is depicted in FIG. 4, where the spacer molecule is linked to the ionophore (gramicidin) via a carbamate linkage and linked to the thiosulfonate moiety via an amide linkage. The carbamate and amide linkages are in general more resistant to hydrolytic decomposition than an ester bond.

FIG. 4 shows the preparation of a thiolsulfonate-activated ionopohore (gramicidin-EO$_3$-N-succ-EO$_4$-EO$_3$-C$_4$-MTS) having a hydrophilic spacer. Introduction of heteroatoms such as nitrogen (e.g. amines) or oxygen (e.g. ethylene oxides) in the spacer is well known to increase the water solubility in comparison with the spacer based on less polar components. The increased water solubility of the spacer in general increases the water solubility of the final conjugate of ionophore-spacer-recognition molecule. This may result in more efficient conjugation or insertion of the conjugate into the membrane. Long aliphatic spacers often have an interaction with the hydrophobic portion of a membrane and thus produce a less available reactive moiety toward the recognition molecule (see Vogt, et al. Biochemistry, 33(8): 2063-7(1994)). Thus, by increasing the water solubility of the spacer, a more exposed reactive moiety is available for conjugation to the recognition molecule.

The present invention is also directed to a conjugate comprising an ionophore, a spacer group, and a recognition molecule, wherein the spacer group covalently links the ionophore to the recognition molecule and the spacer group is linked to the recognition molecule via a disulfide bond.

A recognition molecule suitable for a thiolsulfonate-activated ionophore in general has one or more sulfhydryl groups such that it can covalently attach to the spacer group by a disulfide bond. A recognition molecule can be a small or large molecule such as an antibody, an antibody fragment, an enzyme, an antigen, a lectin, a hapten, an aptamer, a chelating agent and a dye. In one embodiment of the invention, the recognition molecule is a monoclonal or polyclonal antibody or antibody fragment. A preferred antibody fragment is a Fab' or F(ab')$_2$. In one embodiment, the recognition molecule is an antibody or an antibody fragment capable of recognizing and binding to an epitope present in an analyte (or target molecule) such as a virus, a bacterium, a drug, a peptide, an enzyme, a cell, a protein, a hormone, a DNA sequence such as an oligonucleotide, and the like. In another embodiment, the recognition molecule is a peptide and the analyte is an antibody or immunoglobulin, an enzyme or a cell surface recognition site.

The direct linkage of an ionophore to a recognition molecule relies on the formation of a disulfide bond between the thiol-bearing recognition molecule and a thiolsulfonate-activated ionophore. Traditional reagents for thiol modification (maleimides, iodoacetates and mercurials) require long reaction times and large excess of reagent. In contrast, methanethiosulfonate reagents have extremely rapid reactivity under mild conditions and high selectivity. Methanethiosulfonate reagents in general result in quantitative and complete conversion to the disulfide without having to apply a large excess of reagent. The MTS reaction can be performed in anhydrous organic solvents, buffered aqueous, or aqueous-organic solvents. The procedures for preparing an ionophore-MTS reagent are straightforward. The ionophore-MTS reagent can be properly characterized by NMR and Electrospray MS.

In general, the reactivity of MTS reagents with thiols is about $10^4 M^{-1} Sec^{-1}$ to about $10^6 M^{-1} Sec^{-1}$ and more specifically about $10^5 M^{-1}$ sec (Stauffer, D. A. and A. Karlin., Biochemistry 33: 6840-6849, (1994)). Because of the high reactivity, a complete modification can be achieved in a few seconds using reagent concentrations in the 10-100 μM range. In comparison, maleimides in general react with thiols at a much lower rate of about $10^2$-$10^3$ $M^{-1} sec^{-1}$, dependent on pH, ionic strength, and nucleophilicity of the thiol group (Li, et al., PNAS 99:18, 11605-11610 (2002); and Schelte, et al. 2000. Bioconjugate Chem. 11, 118-123 (2000)).

The conjugate of the present invention can be prepared by reacting the activated ionophore with a recognition molecule under proper conditions.

Figure 3:
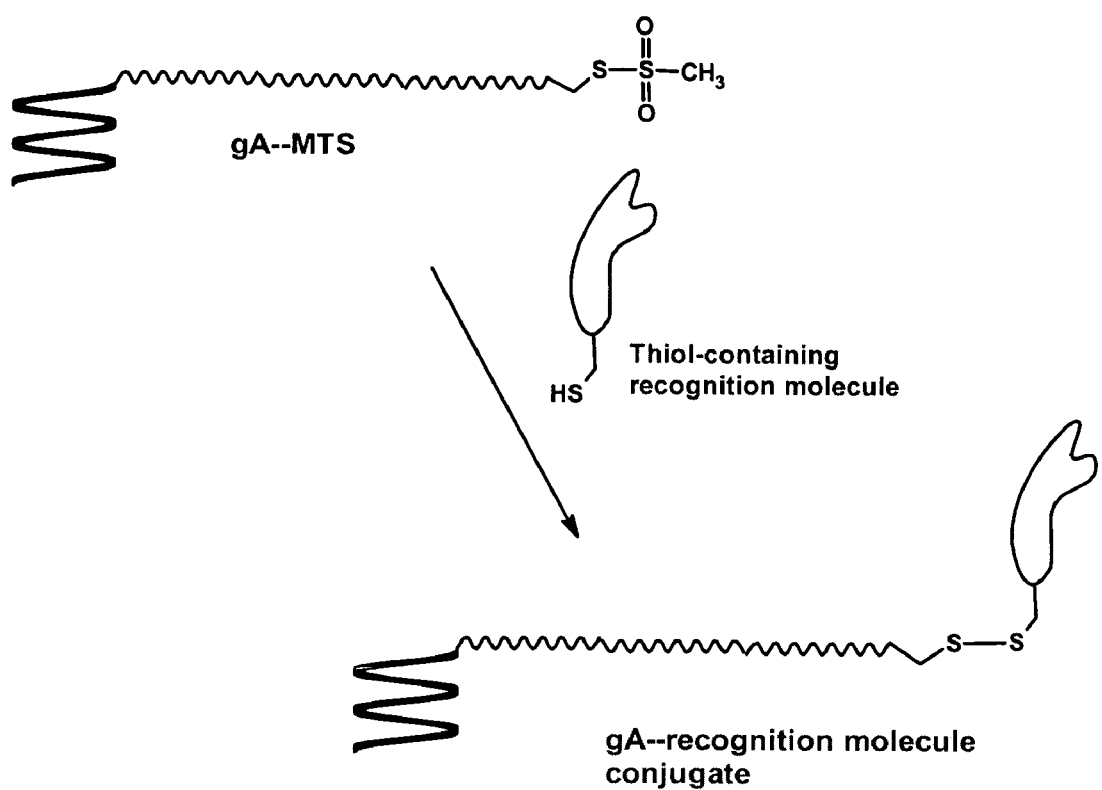
FIG. 3 illustrates the reaction between a recognition molecule having a free sulfhydryl group and a gramicidin-spacer-MTS reagent.

Once the activated ionophore having reactive group is prepared, it can react with a recognition molecule bearing a free sulfhydryl group to form a disulfide bond between the ionophore and the recognition molecule. In this manner, a covalently bonded conjugate of ionophore-spacer-recognition molecule is formed. For example, as shown in FIG. 3, a recognition molecule having a free sulfhydryl (thiol) group can be reacted with a gramicidin (gA)-spacer-MTS moiety to form a conjugate of gramicidin-spacer-recognition molecule. Similar reactions can be carried out in any suitable manner with any suitable recognition molecules. A desired recognition molecule can be modified to bear a free sulfhydryl group if necessary.

As an example, gramicidin-4X-C$_6$-MTS can react with an antibody fragment Fab having a free sulfhydryl group such that gramicidin-4X-C$_6$-Fab is formed (FIG. 1). The reaction can be carried out in ethanol at room temperature.

The methods of the present invention provide covalently bonded ionophore-spacer-recognition molecule conjugates. The conjugates of the present invention exhibit increased stability in comparison with an indirect linkage between ionophore and recognition molecule, e.g., via a biotin-streptavidin interaction.

In one embodiment, the invention is directed to a membrane in which the admittance of the membrane is dependent on the presence or absence of an analyte, the membrane comprising: (a) a first and a second layer each comprising closely packed amphiphilic molecules; a plurality of first ionophores and second ionophores, and (b) a plurality of recognition molecules covalently attached to the second ionophores via a disulfide bond and a spacer group, the recognition molecules being capable of binding to the analyte; wherein the first ionophores are fixed in the first layer and are prevented from lateral diffusion in the first layer; and the second ionophores are located in the second layer and are capable of lateral diffusion within the second layer. The binding of the analyte to the recognition molecules causes a change in the relationship between the first ionophores and the second ionophores such that the flow of ions across the membrane via the first and the second ionophores is allowed or prevented. In one embodiment of the membrane of the present invention, the recognition moieties of the recognition molecules project outwardly from the surface of the second layer such that the binding of the analyte to the recognition molecules is not sterically hindered.

In some embodiments, the amphiphilic molecules are surfactant molecules. Surfactants can be any of the known types, i.e. cationic (e.g. quaternary ammonium salts), anionic (e.g. organosulfonate salts), zwitterionic (e.g. phosphatidyl cholines, phosphatidyl ethanolamines), membrane spanning lipids, or non-ionic (e.g. polyether materials). The amphiphilic molecules optionally contain cross-linkable moieties such as a vinyl, methacrylate, diacetylene, isocyano or styrene group, either in the head group or in the hydrophobic tail, and can be crosslinked. Preferred amphiphilic molecules of the second layer of membrane are phospholipids. In the bilayer membrane of the present invention, the hydrophobic tails of the first and second layers are facing each other inwardly.

Figure 5A:
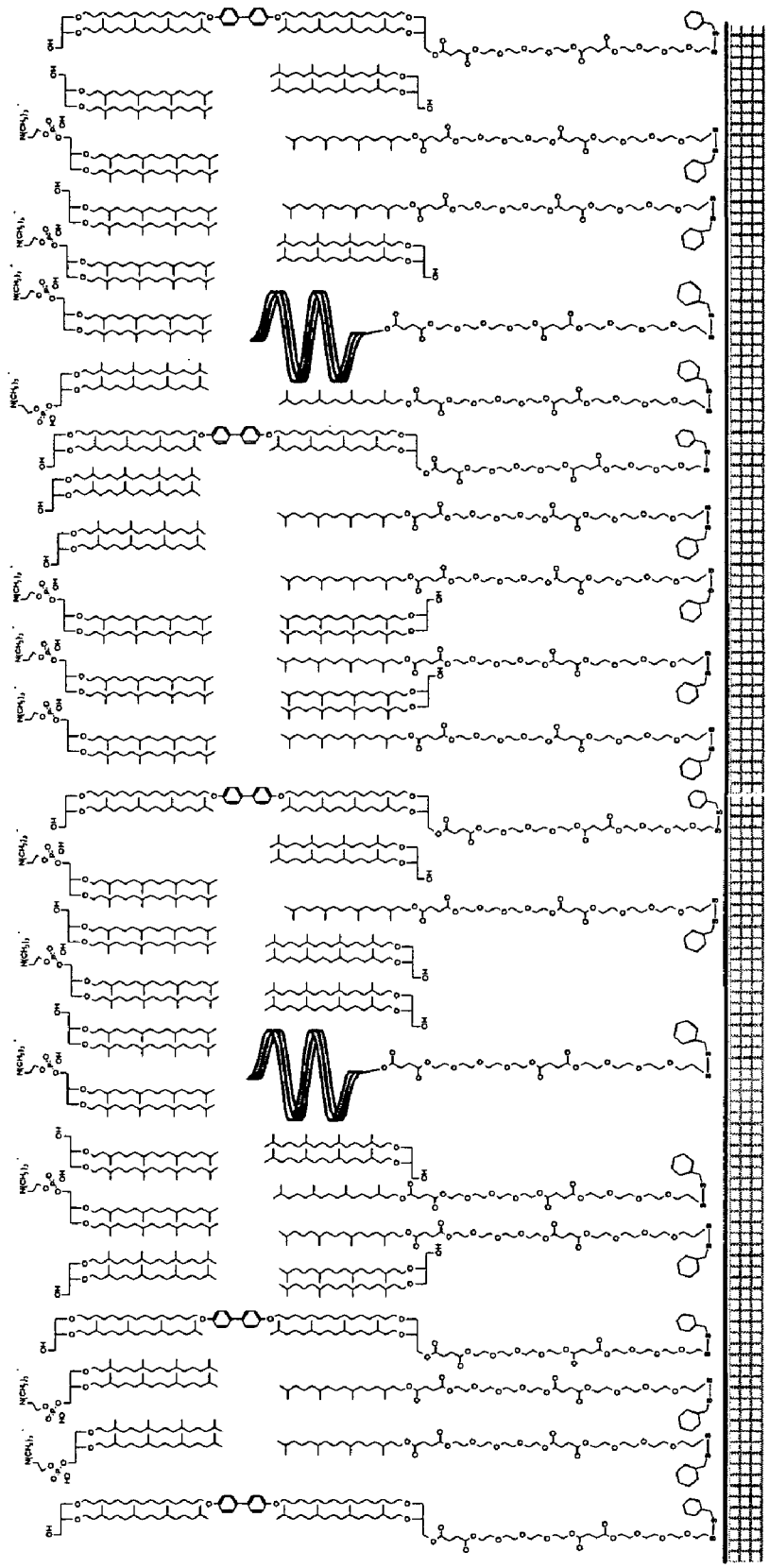
FIG. 5A illustrates a bilayer membrane having the first layer comprising tethered ionophores, and the second layer comprises no ionophore.
Figure 5B:
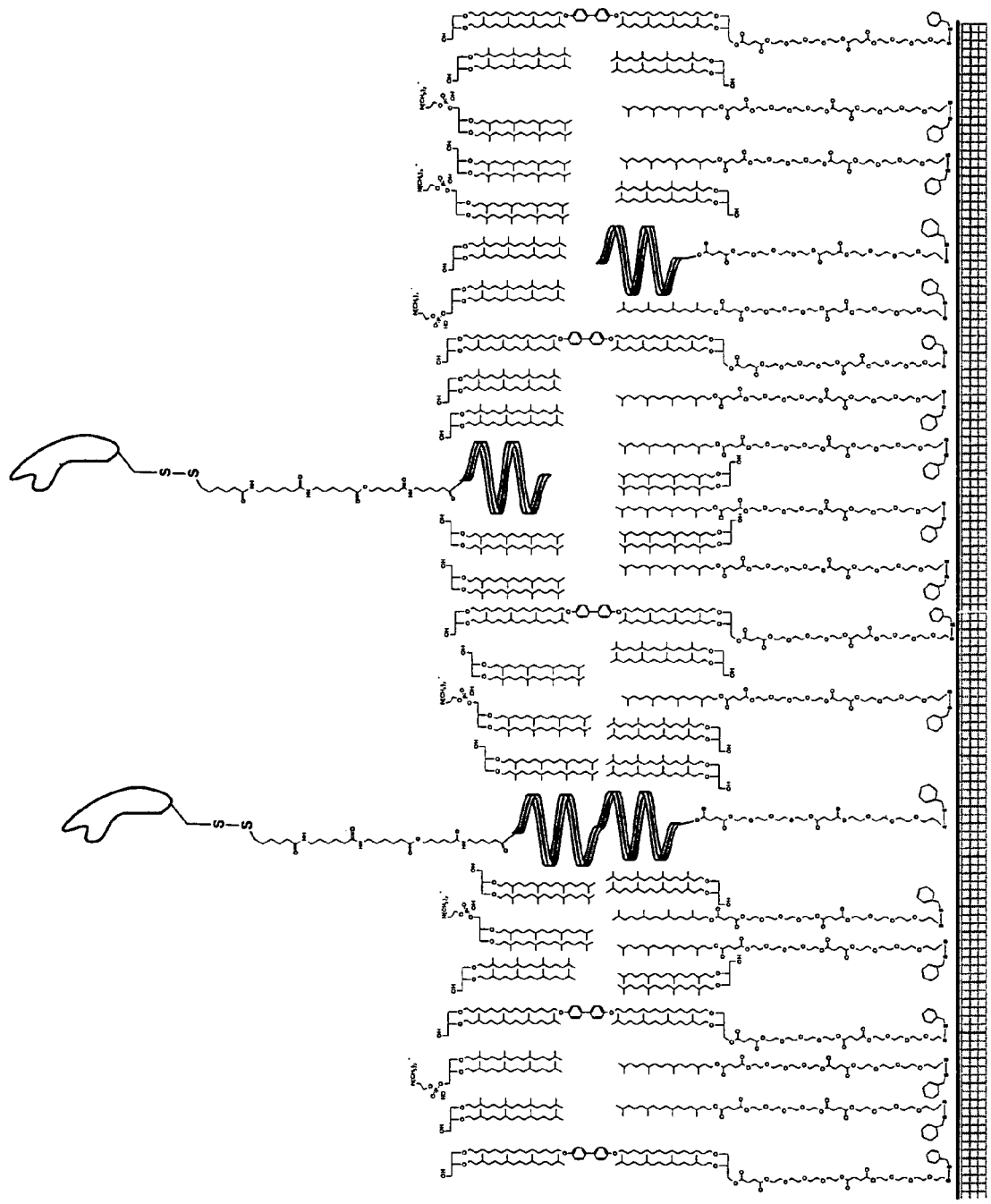
FIG. 5B illustrates the insertion of conjugates comprising ionophore-spacer-recognition molecules into the second layer of the membrane.

The present invention provides various methods for preparing a bilayer membrane that incorporates recognition molecules. One embodiment includes a direct insertion method. In the direct insertion method, the conjugates are formed outside of the membrane, and then are directly inserted into the bilayer membrane. The method comprises the steps of: (a) forming a first layer comprising first amphiphilic molecules and fixed first ionophores, (b) forming a second layer comprising second amphiphilic molecules, (c) contacting the second layer with a plurality of conjugates each comprising a second ionophore, a spacer group, and a recognition molecule, wherein the spacer group covalently links the ionophore to the recognition molecule and the spacer group is linked to the recognition molecule via a disulfide bond. In this method, a lipid bilayer membrane comprising a first layer having tethered first ionophores and a second layer having no ionophore species is pre-formed. Conjugates comprising a second ionophore, a spacer group, and a recognition molecule are separately formed outside of the membrane (FIG. 5A). The conjugates are then incubated with the bilayer membrane such that the conjugates are directly inserted into the second layer with the recognition molecules exposed on the surface of the membrane (FIG. 5B).

The bilayer membrane of the direct insertion method can be formed in any suitable manner. For example, the lipid bilayer can be formed in accordance with the methods detailed in International Application No. PCT/AU98/00417 to Australian Membrane and Biotechnology Research Institute, which is incorporated herein by reference. However, the formation of the second layer of the lipid bilayer is prepared without the ionophore component as taught in International Application No. PCT/AU98/00417. For example, the lipid bilayer may comprise a first layer tethered to a solid substrate, such as a gold substrate or any other suitable substrate, as illustrated in FIG. 5A. The first layer comprises tethered ionophores, and the second layer does not have ionophores.

After the bilayer membrane is formed, a portion of the second layer can be replaced with the ion channel-spacer-recognition molecule conjugates in any suitable manner. For example, the lipid bilayer is subject to rigorous washing and then exposed to a solution comprising the conjugates to insert the conjugates into the lipid bilayer membrane (FIG. 5B). The conjugates of the present invention are particularly suitable for direct insertion into a preformed lipid bilayer membrane. After direct insertion, the recognition molecules are active and ready to react with analytes.

Alternatively, the bilayer membrane incorporating recognition molecules can be prepared by a different method such as in situ conjugation. This method comprises first forming a lipid bilayer, wherein the lipid bilayer comprises a first layer having tethered first ionophores and a second layer having thiol-activated ionophores. Then the lipid bilayer is contacted by recognition molecules having at least one free sulfhydryl group such that conjugates of ionophores and recognition molecules are formed in the second layer of the membrane. In some embodiments, the in situ conjugation method is less preferred because the low concentration of the thiol-activated ionophores in the membrane may cause a less favorable kinetic reaction.

Figure 6A:
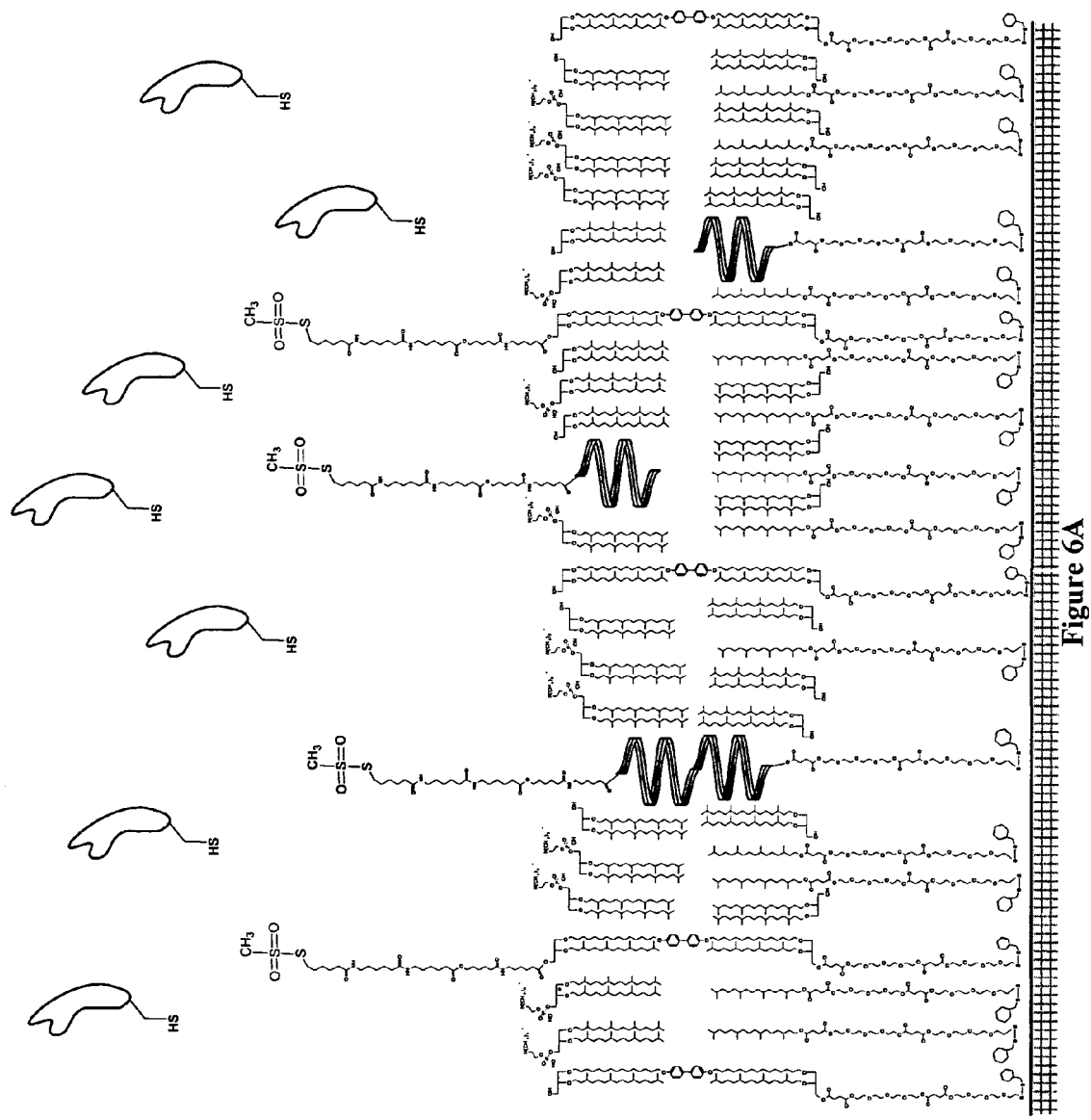
FIG. 6A illustrates a bilayer membrane having the first layer comprising tethered ionophores, and the second layer comprising ionophore-spacer-MTS. The lipid bilayer is exposed to recognition molecules having free sulfhydryl groups.
Figure 6B:
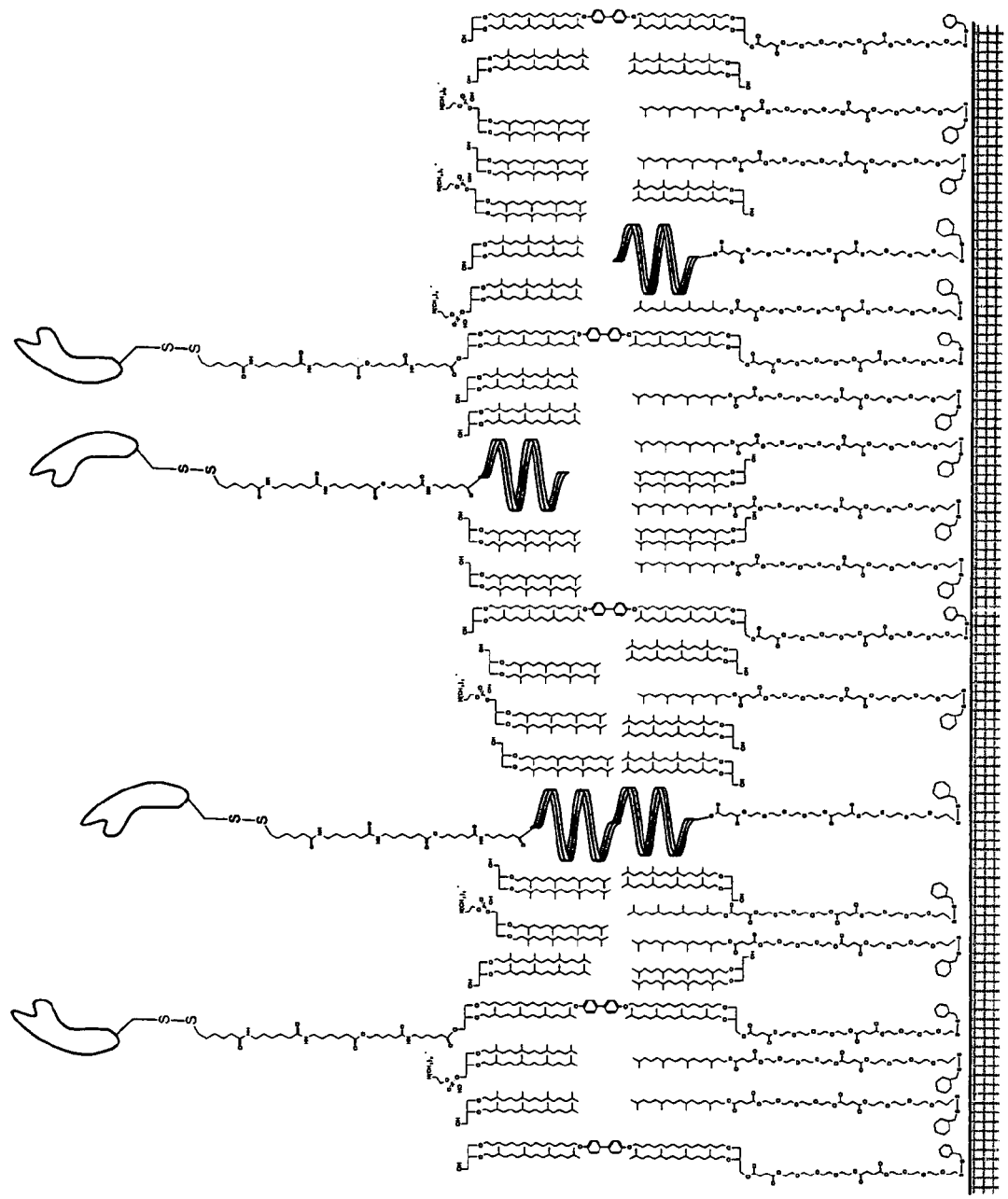
FIG. 6B illustrates the attachment of recognition molecules to the thiosulfonate-activated ionophores in the second layer and incorporation into the bilayer membrane.

The in situ conjugation method is illustrated in FIGS. 6A and 6B. In FIG. 6A, the first lipid layer is tethered to a substrate, such as a gold substrate or any other suitable substrate. The first layer comprises tethered ionophores, and the second layer comprises ionophore-spacer-MTS. The lipid bilayer is exposed to recognition molecules having free sulfhydryl groups. In FIG. 6B, the recognition molecules are attached to ionophores in the second layer and incorporated into the bilayer membrane.

The admittance of the membrane of the present invention is responsive to the binding of the analyte to the recognition molecule. For example, the recognition molecule normally exists in a first state, but it changes to a second state when it binds to an analyte; said change of state causing a change in the ability of ions to pass through the ion channel.

In one embodiment, the first state of the recognition molecule is a state in which the passage of ions through the ion channel is prevented or hindered. Attachment of the analyte to the recognition molecule causes the recognition molecule to enter a second state wherein ions may pass through the ion channel. In this arrangement, an ion channel may be used to detect as little as a single molecule of analyte. The attachment of a single molecule of analyte will cause an ion channel to open and thus cause a leak of ions across the membrane. After a brief time, this ion leak may be detected as the signal for the binding of the analyte to the recognition molecule.

In another embodiment, the first state of the recognition molecule is a state in which the passage of ions through the ion channel is allowed. Attachment of the analyte to the recognition molecule causes the recognition molecule to enter the second state wherein the passage of ions through the ion channel is hindered. For example, in the absence of an analyte, the ionophores in each of the first and second layers align themselves to produce an intact channel, which allows the passage of ions through the membrane. In the presence of an analyte, the ionophores in the second layer bind to an analyte and diffuse out of alignment with the ionophores in the first layer; the misalignment breaks the channel and prevents ions from passing through the membrane. The binding of a single molecule of analyte can cause an intact ion channel to be broken, thus reducing or stopping the flow of ions across the membrane. After a brief time, this change in passage of ions across the membrane can be detected as a signal by measuring the change in either the admittance or impedance. The signal indicates the binding of the analyte to a recognition molecule. The measurement of current flow across membranes due to a single ionophore typically yields a current of about 1-10 pA per channel and preferably about 4 pA per channel.

Methods for measuring the change in admittance or impedance of membranes are comprehensively described in the scientific literature. One method involves the use of black lipid membrane chambers. The method of signal analysis can be a two, three or four terminal impedance measurement in which the frequency characteristics, noise spectra, cyclic voltammetry or statistics on the inherent making or breaking of ion channels are used to characterize changes in admittance through the membrane (see U.S. Pat. No. 5,741,712).

The present invention is also directed to a biosensor comprising the membrane as described above and a solid surface, wherein the membrane is attached to the solid surface in a manner such that a reservoir exits between the membrane and the solid surface. The reservoir serves as a zone or space wherein conductive ions can accumulate. The solid surface is in general conductive and serves as an electrode.

In one embodiment, the membrane is attached to a solid surface via reactive groups on the amphiphilic molecules in the first layer of the membrane. Solid surfaces include hydrogels, ceramics, oxides, glasses, silicon, polymers, and transition metals. Preferred transition metals are gold, platinum and palladium. The attachment of the membrane to a solid surface can be achieved by non-covalent or covalent attachment. For example, vinyl groups on a solid substrate can be copolymerized with a vinyl-terminated lipid. A sulfur-terminated lipid can be adhered to a metal (e.g. gold or palladium) substrate. Condensation or addition reactions can be used to anchor the lipid onto a solid surface. Modification of the solid substrate, if necessary, can be achieved using known techniques such as silylation. Methods of attaching membrane to the solid surface are described, for example, in U.S. Pat. No. 5,741,409, which is incorporated herein by reference.

The biosensor of the present invention can be constructed in a similar fashion as to those described in U.S. Pat. Nos. 6,291,155; 5,401,378 (specifically Example 2 and FIG. 8); and 6,316,273; the contents of which are incorporated herein by reference. In one embodiment, a gold-covered slide is made by sputtering gold onto a suitable substrate such as polycarbonate in a suitable pattern. The slide is then immersed in a suitable organic solution containing a first layer lipids including ionophore, which are chemisorbed onto the gold surface and form a self-assembled monolayer on top of the gold surface. The suitable organic solvent is generally ethanol, decane, hexane, dichloromethane, or any commonly available solvent provided that it does not interact with the substrate. The time of adsorption of the lipid molecules in general varies from a few minutes to many hours. The slide is then rinsed with a suitable organic solvent. After the excess organic solvent is removed, the slide is dried by any suitable means, for example, by nitrogen gas. The dried slide is placed into a metal block. An organic solution containing a second layer lipids is then added to the top of the gold surface and incubated for a suitable time, such as a few minutes to a few hours. The second layer lipids either contain ionophores or do not contain ionophores. After washing the slide with an aqueous solution such as phosphate-buffered saline, a bilayer membrane is formed on top of the gold surface. The resulting biosensor can then be placed in an appropriate impedance bridge for measurements of admittance or impedance.

Tethering a lipid bilayer membrane to an electrode such as a gold electrode provides enhanced stability of a biosensor. Unlike a conventional supported lipid bilayer, a tethered system allows the system to be formulated for an extended storage. The lipid tethering also allows high detection sensitivity due to an ionic reservoir region formed between an electrode and the tethered lipids. Ion flux between the reservoir and the external compartment allows convenient electrical transduction measurement in multi-sensor array format.

The biosensor provides a tool for detecting the presence or absence of an analyte in a sample. In one embodiment, the present invention provides a method for detecting the presence or absence of an analyte in a sample, the method comprises the steps of: (a) providing a biosensor comprising a membrane incorporating plurality of conjugates each includes an ionophore, a spacer group, and a recognition molecule, wherein the spacer group covalently links the ionophore to the recognition molecule and the spacer group is linked to the recognition molecule through a disulfide bond, wherein the recognition molecule is capable of binding to the analyte, (b) contacting the sample with the biosensor and (c) determining the change in the admittance or impedance of the membrane. In some embodiments, admittance or impedance is determined at various intervals after the contacting, for example, at intervals of seconds or minutes when the binding reaction between the analyte and recognition molecule is in still progress and is not complete. In other embodiments, impedance or admittance is determined when the binding reaction reaches an equilibrium or a plateau. The measurement of the change in admittance or impedance is influenced by the affinity of the analyte to the recognition molecule. In some preferred embodiments, the contacting time will be for seconds or minutes and the determination of admittance or impedance is made at intervals of seconds or minutes.

In a further embodiment, the present invention provides a method for detecting the presence or absence of an analyte in a sample, the method comprises the steps of: (a) providing a biosensor as described above, wherein the recognition molecules are capable of binding to the analyte, (b) contacting the sample with the biosensor, (c) allowing the binding of the analyte to the recognition molecules, and (d) determining the change in the admittance or impedance of the membrane. In some embodiments, not all analyte molecules will be bound instantaneously by recognition molecules, but binding will occur over time at a rate proportional to the concentration of the analyte. In other embodiments, it is not required that the binding of the analyte to the recognition molecule be a complete binding, thus the change of impedance or admittance can be determined at various intervals. In some embodiments, the reaction rate is measured over a period of seconds, minutes or hours. The reaction time in general depends upon the affinity of the analyte to the recognition molecule.

Samples that will include an analyte, and are suitable for the present invention include body samples and non-body samples. Examples of body samples are blood, serum, sweat, tears, urine, saliva, throat swabs, nasopharyngeal aspirates, smears, bile, gastrointestinal secretions, lymph, and organ aspirates and biopsies. Non-body samples include any solution samples not derived from a human body, for example, culture medium, water, saline, organic acids and buffers. A wide variety of analytes such as hormones, proteins, nucleic acids, drugs, small molecules, microorganisms, electrolytes, antigens, and antibodies can be detected or quantitated by the present invention. The present invention provides a rapid, sensitive, specific, and reproducible method for detecting an analyte.

The present invention is further directed to a device comprising an array of biosensors as described above. Because biosensors measure electrical transduction signals, miniaturization of the device is achievable. The device is useful in that it can measure multiple samples at the same time. In one embodiment, the various biosensors can be arranged within a single device containing identical membranes, and are used to detect the same target molecule (analyte) from various samples. In another embodiment, the various biosensors can be arranged within a single device containing different membranes, and are used to detect a panel of different analytes either from the same sample or from different samples.

In order that the invention may be more readily understood, reference is made to the following examples, which are intended to be illustrative of the invention, but are not intended to be limiting in scope.

EXAMPLES

Example 1

Preparation Gramicidin-4X-$C_6$-MTS

Preparation of O-(N-(N-(N-(N-BOC-6-aminocaproyl)-6-aminocaproyl)-6-aminocaproyl-6-aminocaproyl-)gramicidin (Gramicidin-4X-BOC)

Gramicidin-4X-BOC was prepared in accordance with the procedures described in U.S. Pat. No. 6,210,551.

Preparation of 6-carboxyhexyl methanethiosulfonate ($C_6$-MTS)

6-Bromohexanoic acid (1.0 g, 5.1 mmol) and Sodium Methanethiosulfonate (750 mg, 5.6 mmol, 1.1 eq prepared according to Kenyon and Bruice, Methods Enzymol. (1977), 47, 407-430) were dissolved in 10 mL of dimethylformamide (DMF), warmed to 55° C. and stirred overnight. The reaction mixture was concentrated to syrup and taken up in $CHCl_3$ (30 mL), washed with $H_2O$ (5×50 mL) and the organic phase was dried with anhydrous sodium sulfate. Concentration by rotary evaporation and elimination of residual solvent with high vacuum yielded 890 mg (78%) of white solid comprising 6-carboxyhexyl methanethiosulfonate. $^1$H NMR: δ 3.31 (s, 3H, $CH_3SO_2S$), 3.16 (t, J=7.5 Hz, 2H, $SCH_2$), 2.37 (t, J=7.2 Hz, 2H, $CH_2COOH$), 1.79 (m, 2H, $CH_2CH_2S$), 1.67 (m, 2H, $CH_2CH_2COOH$), 1.48 (m, 2H).

Preparation of N-Succinimidyloxycarbonylpentyl Methanethiosulfonate (NHS-X-MTS):

6-Bromohexanoic acid (2.80 g, 14.4 mmol) and N-hydroxysucinimide (NHS) (1.82 g, 15.8 mmol, 1.1 eq) were dissolved in 20 mL of Dichloromethane ($CH_2Cl_2$). To this solution, 4.7 g (15.8 mmol, 1.1 eq) of EDC (1-(3-Dimethylaminopropyl)-3-ethylcarbodiimide hydrochloride) were added at once and the solution stirred at) 0 C (ice bath) for 1.5 h followed for overnight stirring at room temperature. The resulting solution was diluted with 75 mL of $CH_2Cl_2$ and washed with 4 portions of 50 ml each of water and once with 50 mL of saturated solution of NaCl. The organic solution was dried with $Na_2SO_4$, concentrated in the rotoevaporator and pumped (high vacuum) overnight to remove traces of solvent to give 3.93 g (93% yield) of a white powder identified as N-succinimidyloxycarbonylpentyl bromide. $^1$H NMR: 3.41 (t, 2H, $CH_2Br$), 2.83 (s, 4H, $CH_2CON$), 2.63 (t, 2H, $CH_2COO$), 1.86 (m, 2H, $CH_2CH_2Br$), 1.79 (m, 2H, $CH_2CH_2COO$), 1.60 (m, 2H).

The succinimidyl derivative (1.0 g, 3.42 mmol) was converted into the methanethiosulfonate reagent by mixing with sodium methanethiosulfonate (0.5 g, 3.73 mmol, 1.1 eq) in 10 mL of dry dimethylformamide (DMF) at 40 C for 16 h. The final compound was isolated by dissolving the DMF solution in 120 mL of Chloroform, washing 6 times to organic phase with about 80 mL of water, dried with solid anhydrous $Na_2SO_4$, concentrating to a syrup and overnight high vacuum pumping of the residue. A waxy white solid (1.02 g, 92% yield) was obtained and identified as N-succinimidyloxycarbonylpentyl Methanethiosulfonate. $^1H$ NMR: δ 3.32 (s, 3H, $CH_3SO_2S$), 3.18 (t, 2H, $SCH_2$), 2.83 (s, 4H, $CH_2CON$), 2.63 (t, 2H, $CH_2COON$), 1.79 (m, 4H, $CH_2CH_2S$, $CH_2CH_2COO$), 1.56 (m, 2H).

Deprotection of gA-4X-BOC gA4XBOC (200 mg, 0.082 mmol) was deprotected by mixing with 3 mL of trifluoroacetic acid (TFA) for 10 min at room temperature. The slightly purple solution was concentrated and co-evaporated 3 times with toluene (5 mL) to eliminate residual TFA. The resulting oil was re-dissolved in a Methanol/Chloroform mixture (25/75) and brought to pH 8 (pH paper) using triethylamine. The solvents were evaporated and residual solvent removed by co-evaporation with toluene (2×10 mL) and dried under high vacuum for 1-2 h to give an oily residue that was used without further purification to the next step. The removal of the t-BOC was confirmed by the disappearance of the large singlet at δ 1.35 ppm in the $^1H$ NMR of the residue.

Preparation of gA-4X-$C_6$-MTS

The oily residue was re-dissolved in 5 mL of dry DMF, mixed with 120 mg of 6-carboxyhexyl methanethiosulfonate (120 mg, 0.53 mmol, 6.6 eq), 1 mL of 1M DCC in $CH_2Cl_2$ (Aldrich, 1 mmol) and 30 mg (0.246 mmol) of DMAP. The reaction mixture was warmed to 40° C. and stirred under Argon for 18 hours. A small amount of precipitate was removed by a filtration through a small cotton plug and the resulting solution was concentrated to approximately 2 mL and purified by size exclusion chromatography (LH-20) using methanol as the eluent. Collection and concentration of fractions showing UV activity yielded gramicidin-5X-MTS (208 mg). Electrospray MS (positive mode, methanol with 0.1% formic acid as eluent) gave a distinctive peak m/z 1294 (corresponding to the sodium adduct of doubly charged ion, 2542 Da, theoretical 2543 Da).

Example 2

Preparation of Conjugates of Gramicidin-Fab' Against hCG

Preparation of Fab'

$F(ab)'_2$ antibodies specific for hCG (Biodesign lot # 525.05-06) were purchased from Strategic Biosolutions (Newark, Del., USA) as a 0.53 mg/ml solution in 20 mM sodium phosphate buffer, 150 mM Sodium Chloride, 0.05% sodium azide, pH 7.2. Production of thiol containing Fab' was achieved by reduction of the $F(ab)'_2$ using mercaptoethylamine as follows.

The buffer of $F(ab)'_2$ solution (2 mL) was exchanged to 100 mM sodium phosphate buffer, supplemented with 5 mM ethylendiamino tetraacetic acid (EDTA), pH 6.0 by repeated concentration (3 times) to a small volume, followed by reconstitution to initial volume on the desired buffer using 2 membrane centrifugal concentrators of 10 KDa molecular weight cut off (MWCO) (Nanosep® centrifugal device 10K omega Pall Corporation, East Hills, N.Y.). The resulting solution was transferred to a low binding 1.5 mL eppendorf tube and its volume adjusted to a final volume of 200 μL. 20 μL of 0.5 M solution of 2-mercaptoethylamine hydrochloride (Pierce Biotechnology Inc., Rockford, Ill.) was added to the $F(ab)'_2$ solution and incubated at 37 C fro 1.5 h. A slightly cloudy solution was obtained.

Preparation of gA-4X-$C_6$-Fab' Conjugate

The reduced F(ab)'2 was centrifuged at 14,000 rpm for 5 min to sediment the solid residue. The supernatant was transferred to a 0.5 mL centrifugal concentrator of 30K MWCO (Vivaspin®, Vivascience, Hanover, Germany) and the reducing buffer was exchanged to a coupling buffer (140 mM N-Cyclohexyl-2-aminoethanesulfonic acid (CHES), 5 mM EDTA) by repeated concentration (3 times).

A 1.5 mM solution of gA-4X-$C_6$-MTS reagent was prepared in ethanol. A total volume of 40 μL of this reagent was incorporated in 2 additions over a period of 0.5 hours to 160 μL of the solution containing the reduced Fab' (final volume 200 μL) in a low binding Eppendorf vial. A precipitate was observed upon addition of the gA-MTS reagent at room temperature. The resulting suspension was mixed using an end-over-end rotator apparatus. The reaction was stopped by removing the precipitate by centrifugation at 14000 rpm for 5 min. The supernatant was exchanged to a final storage buffer (PBS pH 7.2) by using a centrifugal concentrator (30K MWCO). The final concentration of gA-Fab' was estimated to be 0.3 mg/ml.

Characterization of Fab' and gA-Fab' Conjugate

Equipment—Size exclusion HPLC (SEC) was performed on an Agilent 1100 HPLC system (Agilent, Calif.) using a Shodex KW-803 protein column (300×7.8 mm). Electrospray LC/MS was performed on a Surveyor HPLC system interfaced to a Quantum TSQ triple quadrupole mass spectrometer (Thermo Finnegan, San Jose Calif.) operating in positive mode. The column used was an Agilent Zorbax SB300 C4 column (199×2.1 mm). MALDI mass spectrometry was performed on an Applied Biosystems (Foster City, Calif.) Voyager operating in positive mode.

(i) SEC Analysis of Reduced F(ab)' Fragment

The reduction of $F(ab)'_2$ antibody to F(ab)' fragments was confirmed through analysis of an aliquot (2 μL) of the reaction mixture by size exclusion chromatography on a Shodex KW-803 (30×7.8 mm) protein column eluted at 0.5 ml/min using phosphate-buffered saline (PBS) buffer at room temperature (23 C). Detection was at 280 mm. The unreduced $F(ab)'_2$ antibody eluted at 17.8 minutes under these conditions, whereas the reduced F(ab)' fragment present after incubation with MEA eluted at 19.5 minutes.

(ii) LC/MS Analysis of F(ab)'-SS-5X-gA Conjugate.

An aliquot (5 μL) of the buffer exchanged reaction mixture following conjugation was diluted 5-fold into 20 mM phosphate buffer, pH 7.4. An aliquot (5 μL) of the diluted sample was injected onto a Zorbax SB300 C4 column (100×2.1 mm) and eluted at 0.4 mL/min. Solvent A was water and solvent B was 90% acetonitrile. Both solvent A and solvent B contained 0.1% formic acid. Solvent ratios were initially 95% A and 5% B held until 3 minutes, changed to 110% A and 90% B at 8 minutes and held until 10 minutes. The ratios were then returned to 95% A and 5% B at 12 minutes until completion of the program at 15 minutes. Under these conditions, the unmodified F(ab)' fragment eluted at 3.94 minutes and the modified F(ab)' fragment shortly thereafter at 4.2 minutes. The mass of the conjugate was determined to be 51,730 DA and shown as a distinct peak in the deconvoluted Electrospray MS. This is consistent with the expected value (51,764+/−100 Da) calculated from the mass of the unmodified F(ab)' observed by MALDI MS (49,300+/−100 Da) and the calculated mass of the linker (2464 Da).

Example 3

Preparation of gA-EO$_3$-N-succ-EO$_4$-EO$_3$-C$_4$-MTS

Preparation of Carbamate-linked Gramicidin Derivative with 4,7,10-trioxa-1,13-tridecanediamine (gA-EO$_3$-NH$_2$)

The procedure for preparing this compound is an adaptation of the procedure described by Wooley et al. (Biochim. Biophys. Acta, (1995) 1234, 133-138.

Commercial Gramicidin D (Sigma Chemical Co., 228 mg, 120 µmol), was esterified (2 h, 4 C) with p-nitrophenylchloroformate (Sigma Chemical Co., 242 mg, 1200 µmol) in dry tetrahydrofurane (THF) under Argon gas with slow addition of triethylamine (Aldrich Chemical Co., 600 µL). The resulting carbonate ester was filtered through celite in a sintered glass funnel into a 100-fold excess of 4,7,10-trioxa-1,13-tridecanediamine (Aldrich, 2.64 mL, 12 mmol). The product was purified by gel-filtration on LH-20 in Methanol followed by Centrifugal Chromatography on silica using chloroform:methanol:water (65:25:4) as eluent to give 149 mg (58% yield) of the desired product. TLC, (chloroform:methanol:water, 65:25:4), Rf=0.41, gave a single spot. Electrospray MS (positive mode, methanol with 0.1% formic acid as eluent) gave m/z 1076.1 (theoretical for doubly charged gA-EO$_3$-NH$_2$+H$^+$+Na$^+$=1075.5).

Preparation of Hemisuccinimide Derivative of gA-EO$_3$-NH$_2$: gA-EO$_3$-N-succ

A 20 µmol/mL solution of gA-dPEG$_3$-NH$_2$ was prepared on dry DMF. 1 mL of this solution (44.5 mg, 20 µmol) was mixed with 20 mg of succinic anhydride (Aldrich) and stirred at room temperature under Argon gas. After one hour 200 µl of triethylamine was added and the mixture stirred for another hour. The reaction was quenched by addition of 200 µL of H$_2$O, followed by 100 µL formic acid to convert to the free acid, and purified by gel-permeation chromatography on LH-20 (methanol) to give 39 mg (83% yield) of the hemisuccinate derivative. TLC (chloroform:methanol:water, 65:25:4) gave a single spot, Rf=0.41. Electospray MS (positive mode, methanol with 0.1% formic acid as eluent) gave 1137.2 (theoretical for doubly charged gA-dPEG$_3$-COOH+2Na$^+$=1136.7).

Preparation of N-(4,7,10-trioxa-13-tridecane-N-t-Butyloxycarbonylamide)butyl(4-thiomethylsulfonyl)amide(N-t-BOC-EO$_3$-C$_4$-MTS)

N-succinimidyl-oxycarbonylpropyl-methanethiosulfonate (NHS-C$_4$-MTS) was prepared from commercially available bromobutyric acid, N-hydroxysuccinimide and sodium methanethiosulfonate in a similar fashion as the bromohexanoic acid homologue described in Example 1. t-Butyl-oxy-carbonyl-N-(4,7,10-trioxa-1,13-tridecanediamine) carbamate (N-t-BOC-dPEG$_3$-NH$_2$: Mono-N-t-BOC-dPEG3-amine was purchased from Quanta Biodesign, (Powell, Ohio).

The mono-t-BOC protected diamine (1.0 g, 3.12 mmol), 400 µl of triethylamine and NHS-C$_4$-MTS (1.2 g, 4.08 mmol, 1.3 eq.) were dissolved in 10 mL of dichloromethane at room temperature under Argon gas and stirred overnight. The resulting mixture was concentrated to a small volume and purified directly using Centrifugal Chromatography (chloroform:methanol, 250:3 to 250:10) to give 1.51 g (96% yield) of an oily residue. Electrospray MS (positive mode, methanol with 0.1% formic acid as eluent) gave m/z 523.4 (theoretical for N-t-BOC-EO$_3$-C$_4$-MTS+Na$^+$=523.6) $^1$H NMR and $^{13}$C NMR also showed the expected signals.

Preparation of N-(4,7,10-trioxa-13-tridecaneamine)butyl(4-thiomethylsulfonyl)amide (H$_2$N-EO$_3$-C$_4$-MTS)

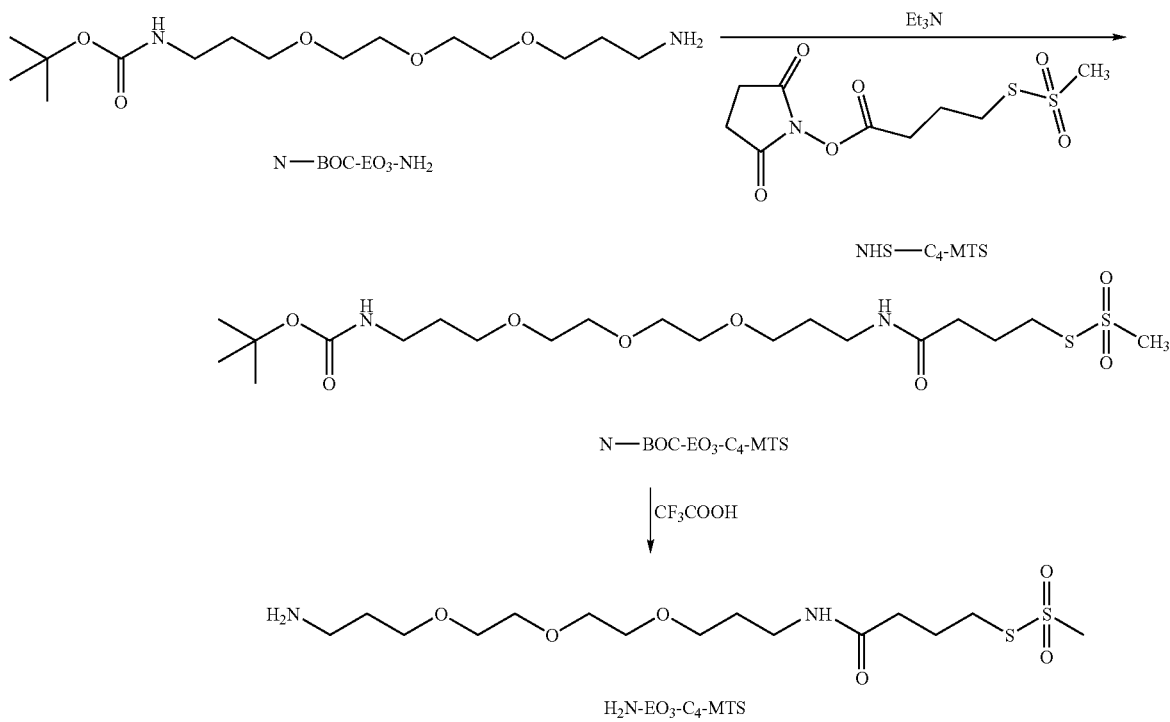

The amino protecting group of N-t-BOC-EO$_3$-C4-MTS (700 mg) was removed by mixing the MTS derivative with 3 mL of trifluoroacetic acid at room temperature for 30 minutes under Argon gas. The excess trifluoroacetic acid was removed by high vacuum concentration using a rotoevaporator followed by two times co-evaporation (rotoevaporator) with toluene at high vacuum. The oily residue (550 mg, 97% yield) was pumped overnight to give the desired product. 1H NMR analysis showed the removal of the t-BOC group by the collapse of the t-BOC signal at 1.43 ppm. Other signals of the spectrum showed no significant modification comparing with the ones corresponding to the protected starting material.

Preparation of N-BOC-EO$_4$-NHS

Commercially available N-BOC-EO$_4$-COOH (2.00 g, 5.4 mmol, Quanta Biodesign, Powell, Ohio) was mixed with N-hydroxysuccinimide (0.69 g, 6 mmol, Aldrich), 4,4-dimethylaminopyridine (0.12 g, 0.97 mmol) and EDC (1.29 mg, 6.48 mmol) in 20 mL of dichloromethane at room temperature. After overnight stirring, the solvent was evaporated and the residue re-dissolved in chloroform (100 mL) and washed with water (2×50 mL), 1N hydrochloric acid (2×50 mL), and saturated NaCl solution (50 mL). The organic phase was dried with anhydrous sodium sulfate and the solvent removed using a rotoevaporator and a vacuum pump to give 2.1 g (83% yield) of a white solid identified by $^1$H NMR as the desired product.

Preparation of N-BOC-EO$_4$-EO$_3$-C$_4$-MTS

H$_2$N-EO$_3$-C$_4$-MTS ((0.6 g, 1.5 mmol) in 5 mL of dichloromethane, BOC-EO$_4$-NHS (0.9 g, 1.95 mmol) in 5 mL of Dichloromethane and 300 µL of triethylamine were mixed at room temperature under Argon gas. After overnight stirring, the reaction mixture was diluted in Chloroform (100 mL) and washed with Water (2×50 mL), 1N Hydrochloric acid (2×50 mL) Saturated NaCl solution (50 mL). The organic phase was dried with anhydrous sodium sulfate and the solvent removed using a rotoevaporator and a vacuum pump. Further purification by Centrifugal Chromatography (chloroform:methanol, 230:20) afforded the desired coupling product (0.78 g, 70% yield) which was confirmed by $^1$H NMR and MS. Electrospray MS (positive mode, methanol with 0.1% formic acid as eluent) gave 770.6 (theoretical for t-BOC-dPEG$_4$-dPEG3-C$_4$-MTS+Na$^+$=770.96) $^1$H NMR also showed the expected signals.

Preparation of H$_2$N-EO$_4$-EO$_3$-C$_4$-MTS

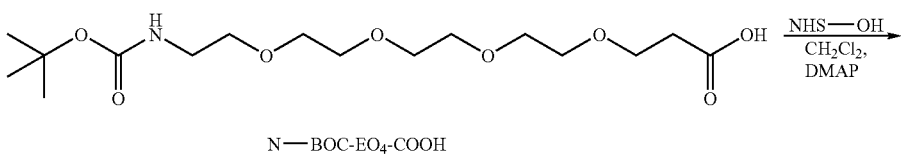

N—BOC-EO$_4$-COOH

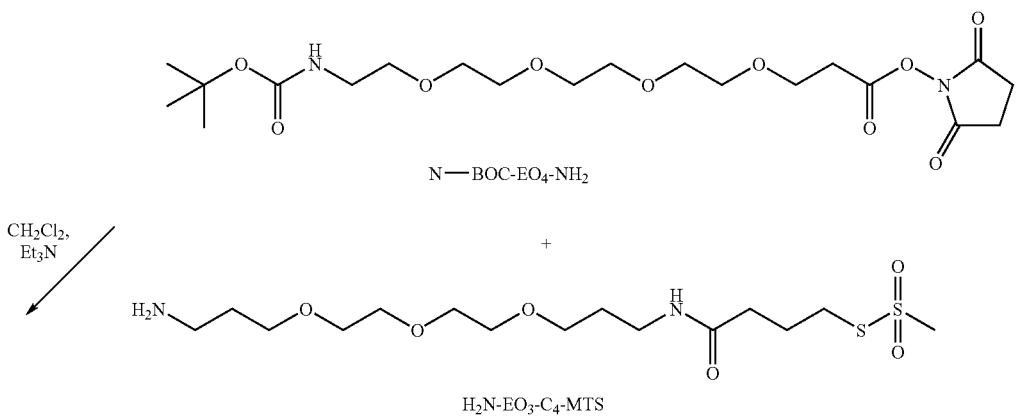

N—BOC-EO$_4$-NH$_2$

H$_2$N-EO$_3$-C$_4$-MTS

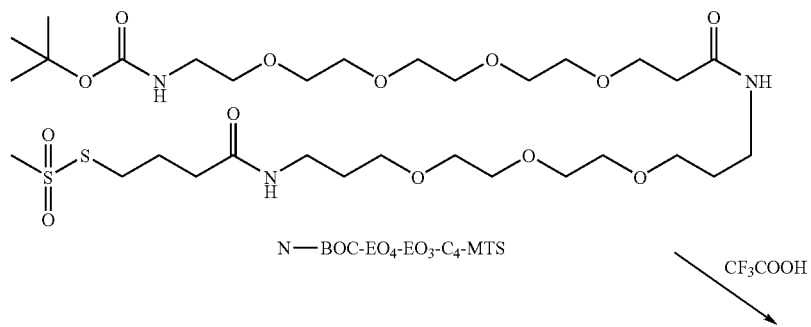

N—BOC-EO$_4$-EO$_3$-C$_4$-MTS

-continued

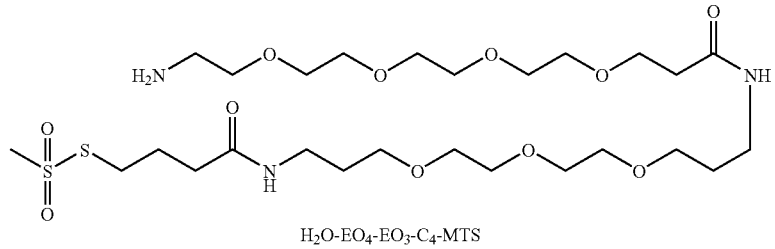

H₂O-EO₄-EO₃-C₄-MTS

The amino protecting group of BOC-EO₄-EO₃-C₄-MTS (750 mg) was removed by mixing the MTS derivative with 3 mL of trifluoroacetic acid at room temperature for 30 minutes under Argon gas. The excess trifluoroacetic acid was removed by high vacuum concentration using a rotoevaporator followed by two times co-evaporation (rotoevaporator) 10 with toluene at high vacuum. The oily residue was pumped overnight to give the desired product. ¹H NMR analysis showed the removal of the t-BOC group by the collapse of the t-BOC signal at 1.43 ppm. Other signals of the spectrum showed no significant modification comparing with the ones corresponding to the protected starting material.

Preparation of gA-EO₃-N-succ-EO₄-EO₃-C₄-MTS

To a solution of gA-EO₃-N-succ (32 mg, 14 mmol) in 1 mL anhydrous DMF, 100 µL of a 19 mg/mL solution of N-hydroxysuccinamide in DMF (1.9 mg, 17 µmol) was added. The mixture was stirred and cooled to 0° C. under Argon gas before adding 100 µL of a 32 mg/mL solution of 1-ethyl-3-(3-dimethylaminopropyl)-carbodiimide in DMF (3.2 mg, 31 µmol). After stirring for 48 hours, the mixture was again cooled to 0° C. under Argon gas and 412 µL of a 44 mg/mL solution of H₂N-EO₄-EO₃-C₄-MTS in DMF (18.1 mg, 28 µmol) added. After stirring 48 hours, the reaction mixture was purified by gel-filtration on LH-20 in Methanol followed by Centrifugal Chromatography on silica using chloroform:methanol:water (65:25:4) as eluent to give ca. 1 mg (2.5% yield) of the desired product. TLC (chloroform:methanol:water, 65:25:4), Rf=0.75, gave a single spot. Electrospray MS (positive mode, methanol with 0.1% formic acid as eluent) gave 1451.9 (theoretical for doubly charged gA-EO₃-N-succ-EO₄-EO₃-C₄-MTS+2Na⁺= 1451.3).

Example 4

Response of Sensor in the Presence of an Analyte

A gA-Fab conjugate was incorporated into a membrane in accordance with the following methods.

Preparation of Membrane on Electrode

The supported membrane for use in detecting the analyte was constructed in a similar fashion as to one described in U.S. Pat. No. 6,291,155B1. Also reference is made to U.S. Pat. No. 5,401,378, specifically Example 2 and FIG. 8. Briefly, a gold-covered slide was made by sputtering gold onto a suitable substrate such as polycarbonate in a suitable pattern. The slide was then immersed in an ethanol solution containing the first layer lipids including ionophore, which were chemisorbed onto the gold surface to give a self-assembled monolayer. The time of absorption of the lipid molecules was typically 24 hours. The slide was then rinsed with ethanol, dried with nitrogen gas and clamped into a metal block containing TEFLON®-coated wells, which defined the area of the working electrode as approximately 16 mm² (Hamilton block). An ethanol solution containing the second layer lipids (2.1 mM 1,2-Di-O-Phytanyl-sn-Glycero-3-Phosphocholine (DPEPC, Avanti Polar Lipids, Alabaster, Ala.), and 0.9 mM 1,2-Di-O-Phytanyl-sn-Glycerol (GDPE, Avanti Polar Lipids, Alabaster, Ala.)), was then added to the top of the working electrode, incubated for up to two minutes, and rinsed with phosphate-buffered saline (PBS, 6.26 mM NaCl, 59.4 mM NaHPO₄.2H₂O, 2.53 mM Na₂HPO₄.12H₂O, 50 mM EDTA at pH 7.4). The electrode was then washed 3 times with PBS and placed in an appropriate impedance bridge for conductivity measurements. Initial measurements of admittance showed that the membrane was barely conductive.

Insertion of gA-Fab' Conjugate

Figure 7:
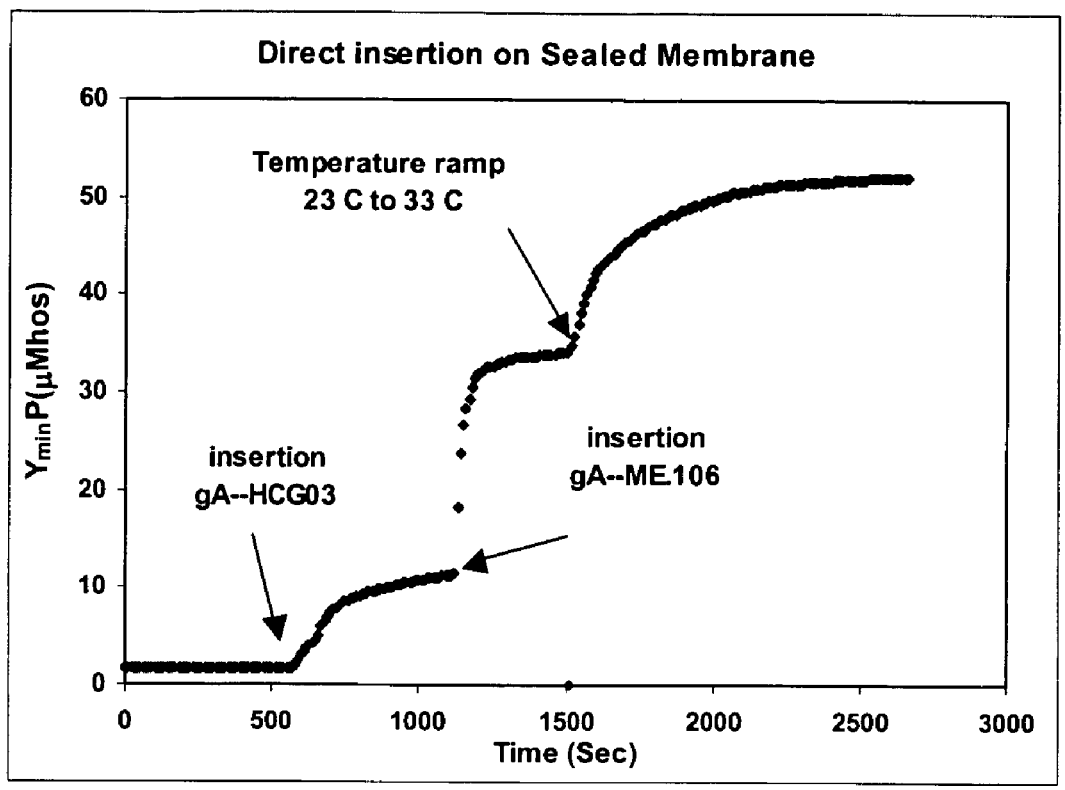
FIG. 7 illustrates the change in admittance (Y in μMhos) at minimum phase observed during direct insertion of gA-Fab' conjugates (gA-HCG03) followed by gA-ME.106 and temperature equilibration. Reference is made to Example 4.

A 100 fold dilution of the gA-Fab' conjugate final solution (Example 2) was prepared in PBS buffer. The conjugate was 'inserted' in the membrane by rapidly mixing 10 µl of the diluted solution with the supernatant solution of the working electrode (100 µL PBS buffer). The mixture was incubated for 20 min at room temperature, then the membrane was washed 3 times with a 0.02% solution of bovine serum albumin in PBS buffer. The insertion of gA-conjugated was confirmed by observing the impedance parameters (admittance at minimum phase) of the assembled sensor. The process was repeated with a different (complementary) gA-Fab' conjugate. Finally the sensor was equilibrated to 33° C. prior to challenging with an analyte (FIG. 7).

Response of Sensor in Presence of hCG

Figure 8A:
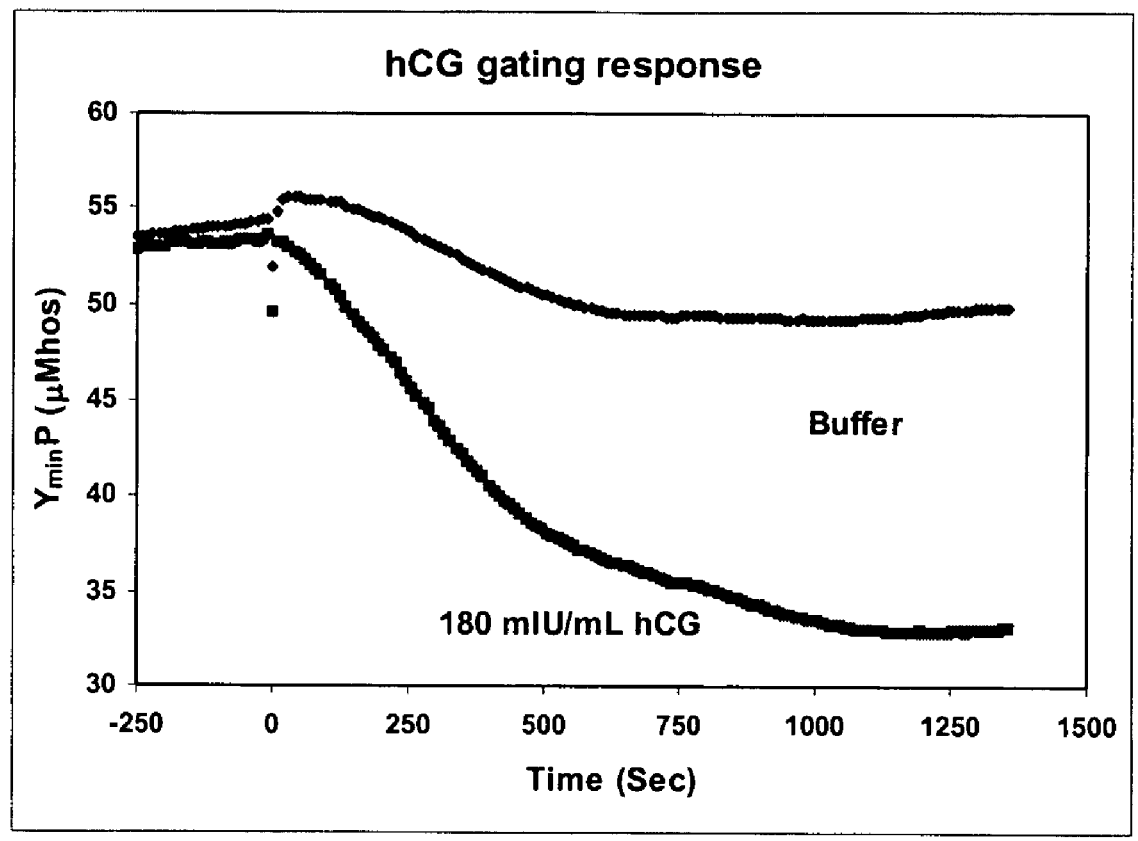
FIG. 8A illustrates the effect of hCG analyte and of buffer on the biosensor.
Figure 8B:
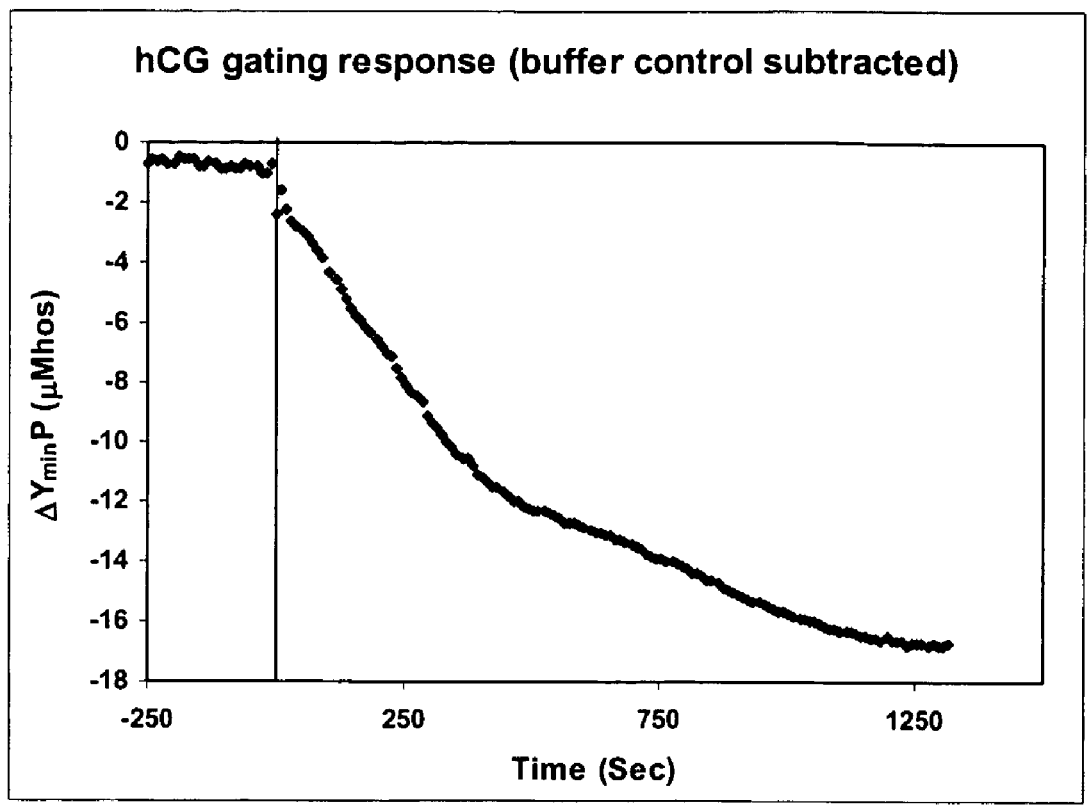
FIG. 8B illustrates the gating response upon addition of hCG analyte.

The sensor built as described above was challenged with 10 µL of solution containing analyte (180 mIU/mL human chorionic gonodotropin (hCG). Admittance parameters at minimum phase were recorded during approximately 20 minutes. As a control, the same volume of a PBS buffer containing no analyte was added to the sensor. The expected decrease in admittance is shown in FIG. 8a and FIG. 8b.

It will be obvious to those skilled in the art that various changes may be made without departing from the scope of the invention, which is not to be considered limited to what is described in the specification.

What is claimed is:

1. A thiosulfonate-activated ionophore comprising an ionophore, a spacer group, and an alkylthiosulfonate moiety, wherein the spacer group covalently links the ionophore to the alkylthiosulfonate moiety.

2. The thiosulfonate-activated ionophore according to claim 1, wherein the ionophore is selected from the group consisting of gramicidin, band three protein, bacteriorhodopsin, proteorhodopsin, mellitin, alamethicin, an alamethicin analogue, porin, tyrocidine, tyrothricin, and valinomycin.

3. The thiosulfonate-activated ionophore according to claim 2, wherein the gramicidin is gramicidin A, gramicidin B, gramicidin C, gramicidin D, gramicidin GT, gramicidin GM, gramicidin GM⁻, gramicidin GN⁻, and gramicidin A'.

4. The thiosulfonate-activated ionophore according to claim 3, wherein the gramicidin is gramicidin A.

5. The thiosulfonate-activated ionophore according to claim 1, wherein the spacer group is selected from the group consisting alkyl, alkyl amides, alkyl esters, alkyl carbamates, alkyl carbonates, oligomers of alkylidene glycol, oligomers of ethylene glycol optionally substituted with amides, esters or carbamates, and oligopeptides.

6. The thiosulfonate-activated ionophore according to claim 5, wherein the spacer group is covalently linked to the ionophore through a carbamate molecule or an ester molecule.

7. The thiosulfonate-activated ionophore according to claim 1, wherein the alkylthiosulfonate is methanethiosulfonate.

8. The thiosulfonate-activated ionophore according to claim 1, which is gramicidin-$EO_3$-N-succ-$EO_4$-$EO_3$-$C_4$-MTS, wherein MTS is methanethiosulfonate, $C_4$ is —$(CH_2CO)_3$—, EO is —$(CH_2)_2O$—, and succ is —$OCCH_2CH_2CO$—.

9. The thiosulfonate-activated ionophore according to claim 1, which is gramicidin-4X-$C_6$-MTS, wherein X is —$NH(CH_2)_5COO$—, $C_6$ is —$(CH_2)_5CO$—, and MTS is methanethiosulfonate.

* * * * *